United States Patent [19]

Masaharu et al.

[11] Patent Number: 5,104,523

[45] Date of Patent: * Apr. 14, 1992

[54] GLASS-PLATE SORTING SYSTEM

[75] Inventors: Okafuji Masaharu; Kurashina Isao; Kawamura Hidetoshi, all of Osaka, Japan

[73] Assignee: Nippon Sheet Glass Co., Ltd., Osaka, Japan

[*] Notice: The portion of the term of this patent subsequent to Apr. 3, 2007 has been disclaimed.

[21] Appl. No.: 296,055

[22] PCT Filed: May 19, 1988

[86] PCT No.: PCT/JP88/00473

§ 371 Date: Mar. 6, 1989

§ 102(e) Date: Mar. 6, 1989

[87] PCT Pub. No.: WO88/09310

PCT Pub. Date: Dec. 1, 1988

[30] Foreign Application Priority Data

May 29, 1987 [JP] Japan .................................. 62-131522
May 29, 1987 [JP] Japan .................................. 62-131523

[51] Int. Cl.⁵ .......................... B07C 5/342; B07C 5/36; G01N 21/89
[52] U.S. Cl. ..................................... 209/585; 209/643; 250/572; 356/431; 364/474.09; 364/552

[58] Field of Search .................. 209/585, 643; 83/879, 83/880; 364/473, 474.09, 552, 478, 507; 250/563, 572; 356/429-431, 237, 239

[56] References Cited

U.S. PATENT DOCUMENTS

| | | | |
|---|---|---|---|
| 3,205,740 | 9/1965 | Groves et al. | 364/552 X |
| 3,215,269 | 11/1965 | Walters | 209/643 X |
| 3,246,550 | 4/1966 | Galey et al. | 364/473 X |
| 3,274,390 | 9/1966 | Umbel | 364/474.09 X |
| 3,966,048 | 6/1976 | Nunes et al. | 209/698 X |
| 4,211,132 | 7/1980 | Nichols, III et al. | 364/474.09 X |
| 4,914,309 | 4/1990 | Masaharu et al. | 356/431 X |

Primary Examiner—Michael S. Huppert
Assistant Examiner—Edward M. Macyra
Attorney, Agent, or Firm—McGlew & Tuttle

[57] ABSTRACT

A glass-plate sorting system for sorting glass plates being cut into products having a plurality of quality grades to simultaneously obtain products of desired quality grades. A discriminating-type flaw detector (101) detects the sizes and locations of flaws existing in a glass strip travelling on a line conveyor and transmits flaw data to a control unit (102). The control unit discriminates quality grades of the cut glass plates based on the flaw data. Sorters (110) having lifters (112) and suction conveyors (111) sort products of desired quality grades based on the control by the control unit (102).

7 Claims, 23 Drawing Sheets

D4A
D3A
D2A
D1
D2B
D3B
D4B

GLASS-PLATE SORTING SYSTEM

TECHNICAL FIELD

This invention relates generally to a glass-plate sorting system for sorting glass plates on a glass-plate manufacturing line.

BACKGROUND ART

The manufacture of glass plates generally involves the cutting and sorting glass plates out of a glass strip pulled up from the furnace while the glass strip travels on the line conveyor. In cutting glass plates out of the glass strip, a single-grade sorting system has heretofore been employed where only those glass plates which are above the aimed-at quality are sorted out, with the balance discarded.

The conventional single-grade sorting/cutting system, however, has a disadvantage of poor yields in manufacturing products having strict quality requirements. Glass plates for automotive windshields, for example, are required to be free of flaws, and of a high quality from the viewpoint of safety. In the manufacturing process of glass plates for automotive windshields, therefore, they are inspected for the presence/absence of flaws, and any glass plates in which flaws are found are discarded.

DISCLOSURE OF INVENTION

Glass-plate products have a wide variety of applications ranging from glass plates for photocopying machines, which require high quality, to glass panes for buildings, which may be of lower quality. Consequently, producing glass plates by sorting high-grade products and low-grade ones simultaneously on the glass-plate manufacturing line would lead to glass-plate manufacture at the yield of the low-grade products.

The quality of glass plates from which automotive windshields are obtained is such that a glass plate need not be free of flaws over the entire surface thereof, but only the see-through area thereof, which is critical for the vision of an automobile driver, must be free of flaws. The remaining peripheral areas immediately around the see-through area may have a certain degree of flaws, and the outermost fringe area of the plate, which are usually discarded, may have any types of flaws. In the manufacturing process of automotive windshields, therefore, glass-plate production yield can be improved by obtaining glass plates by detecting the sizes and locations of flaws in glass plates and judging what sizes of flaws would exist in the assumed see-through area, periphery area and fringe area of a glass plate.

In order to implement the above-mentioned method for obtaining glass plates, a discriminating-type flaw detector is needed, which is capable of detecting at high accuracy the types, sizes, locations of flaws in a glass strip, such as bubbles formed by the air bubbles entrapped inside the glass plate, foreign particles remaining in the glass plate, knots formed by the almost molten foreign matter remaining in the glass plate in a shape having a streaming tail, drips formed by the metallic tin existing in the tin bath deposited on the glass plate surface. The present applicant has already developed a discriminating-type flaw detector meeting such a requirement and filed a patent application under the title of "A Discriminating-Type Flaw Detector For Light-Transmitting Plate Materials" on May 27, 1987 (Japanese Patent Application No. 62-128089). This discriminating-type flaw detector is a flying-spot type flaw detector that scans the entire surface of a glass plate with a light spot, detects transmitted light, transmitted and diffused light, reflected light, and reflected and diffused light by means of a plurality of light receptors, and discriminates the sizes and other parameters of flaws based on a combination of detected results.

This invention is designed to improve yield by producing flaw data information representing the types, sizes and locations of flaws, sending the flaw data information to the control unit of the glass-plate sorting system to determine whether the glass plate can be cut in accordance with the quality requirements of the glass plate, using the discriminating-type flaw detector.

Consequently, this invention is concerned with a glass-plate production system for cutting a glass strip travelling on a line conveyor into cut-lengths of glass plates and sorting the cut glass plates in accordance with required quality grades, which comprises a discriminating-type flaw detector that detects flaws on a glass strip and outputs the flaw data information representing the sizes and locations of the flaws, a control unit for discriminating the quality grades of the cut glass plates, and a plurality of sorting units for sorting glass plates of desired quality grades.

The use of the glass-plate sorting system of this invention makes it possible to obtain glass plates of two quality grades by sorting high-grade and low-grade plates. In doing so, the control unit of the glass-plate sorting system automatically discriminates glass plates being cut into high-grade, low-grade and defective ones, based on the flaw data information transmitted from the discriminating-type flaw detector, to sort the high-grade and low-grade ones in the sorting unit and discard the defective ones by the eliminating/discarding unit. Thus, product yield can be improved by sorting, together with the high-grade products, the low-grade products that have heretofore been discarded in the conventional single-grade sorting system.

When the glass-plate sorting system is used in the automotive windshield manufacturing line, product yield can be improved by tracking the flaws in a glass strip detected by the discriminating-type flaw detector, assuming see-through, peripheral and fringe areas of an automotive windshield on the glass plate cut out from the glass strip, and judging the acceptability of the glass plate based on the flaw existing in these areas.

BEST MODE FOR CARRING OUT THE INVENTION

Figure 1:
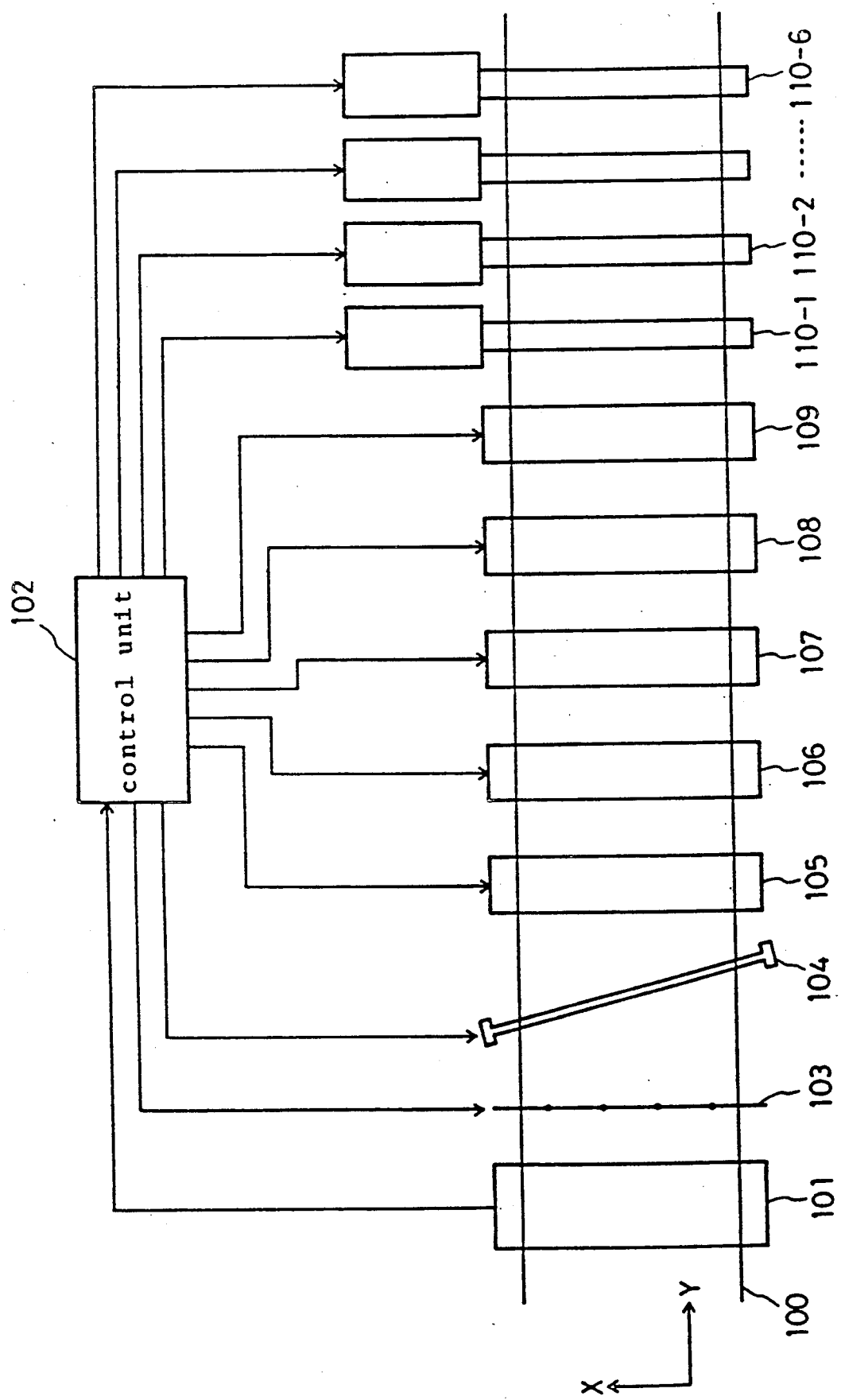
FIG. 1 is a diagram illustrating the construction of a glass-plate sorting system of this invention.

FIG. 1 is a diagram illustrating a glass-plate sorting system of this invention in which a glass-plate manufacturing line ranging from a discriminating-type flaw detector to a glass-plate sorting unit is shown. The manufacturing line has a line conveyor 100 extending in the Y-axis direction, on which a glass strip pulled up from a furnace is transported.

A discriminating-type flaw detector 101 is a flying-spot discriminating-type flaw detector, that scans the glass strip in the X-axis direction, normal to the Y-axis direction, with a light spot to detect flaws present in the glass strip and output flaw data information representing the types, sizes (large-, medium- or small-size) and locations (X, Y) of the detected flaws. The flaw data information thus produced are sent to a control unit 102 comprising a computer, for example.

Upon receipt of the flaw data information from the discriminating-type flaw detector 101, the control unit 102 identifies the sizes and locations of the flaws present in the glass strip, and initiates the tracking of the flaws.

A trimming-line marker 103 marks a plurality of trimming lines in the Y-axis direction at predetermined intervals on the glass strip clearing the discriminating-type flaw detector 101. The trimming-line marker 103 is controlled by the control unit 102 to determine the x-axis locations of the trimming lines.

A diagonal cutter 104 marks a plurality of cutting lines in the X-axis direction at predetermined intervals on the glass strip clearing the trimming-line marker 103. The diagonal cutter 104 has a cutter that travels in the diagonal direction in synchronism with the Y-axis speed of the glass strip. The travelling of the cutter and cutting-line settings are controlled by the control unit 102.

A breaker 105 breaks, or cuts, the glass strip clearing the diagonal cutter 104 along the cutting lines into glass-plate rows. The breaker 105 is of a type that breaks the glass strip while moving up and down on the breaker roll under the control by the control unit 102.

A trimming cutter 106 cuts and removes the trimmings along the trimming lines of the glass-plate rows broken by the breaker 105. The operation of the trimming cutter 106 too is controlled by the control unit 102.

A slitter 107 slits the glass-plate rows along the trimming lines into a plurality of glass plates which are then slightly separated apart by small gaps in the X-axis direction. The slitter 107 too is controlled by the control unit 102.

A separator 108 further separates the slit glass plates in the X-axis direction by the revolution of separating rolls to classify the plates by courses. The operation of the separator 108 too is controlled by the control unit 102.

Figure 2:
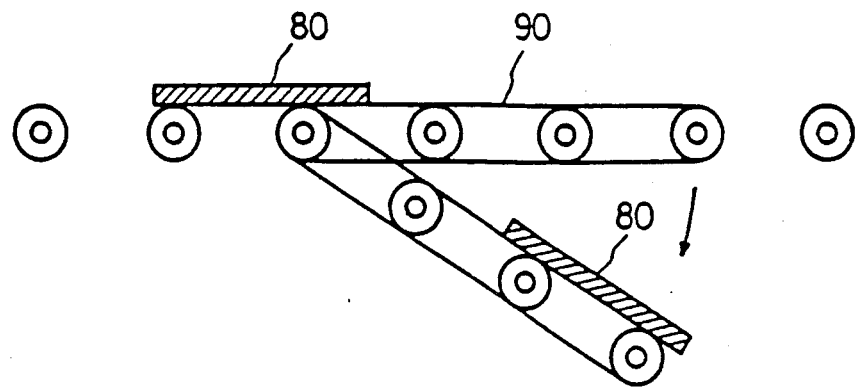
FIG. 2 is a diagram illustrating a discarding roll.

An eliminating/discarding unit 109 has such a construction that defective glass plates can be discarded by each course, based on the control by the control unit 102. FIG. 2 shows the construction of the eliminating/discarding unit for one course, in which as a defective glass plate 80 being discarded comes on a discarding roll 90, the defective plate 80 goes down on the discarding roll 90 for disposal in accordance with the control by the control unit 102.

As indicated by numerals 110-1, 110-2, ---, and 110-6, six units of sorters are provided to sort glass plates based on the control by the control unit 102.

Figure 3:
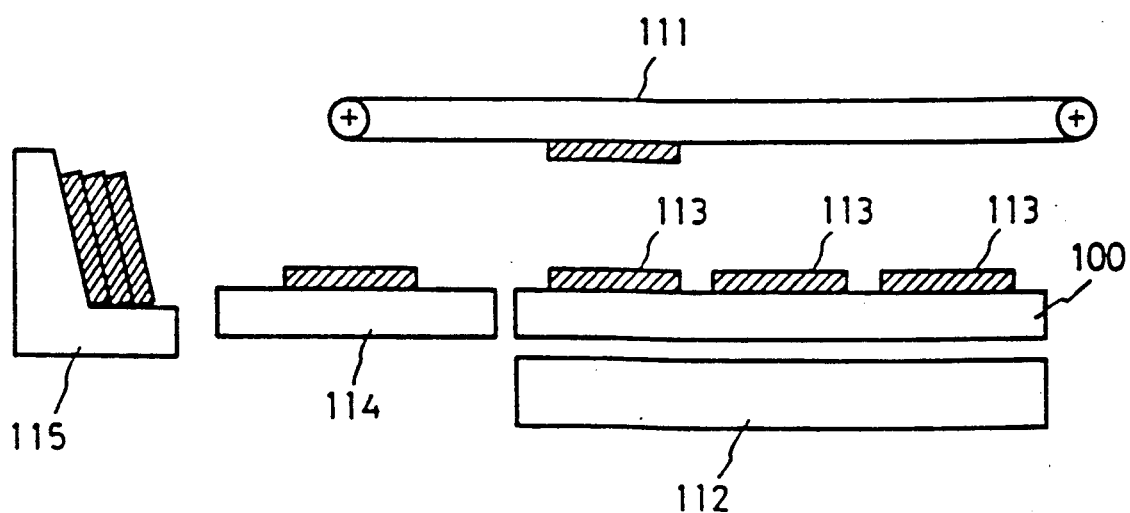
FIG. 3 is a diagram illustrating an example of the construction of a sorter.

FIG. 3 shows the construction of one of the sorters viewed in the Y-axis direction. Above a line conveyor 100 provided is a suction conveyor 111 extending in the X-axis direction, while a lifter 112 is provided below the line conveyor 100. The lifter 112 pushes up the glass plate 113 travelling in the Y-axis direction on the line conveyor 100 based on the control by the control unit 102. The lifting operation by the lifter 112 is controlled in various modes, such as the selective lifting mode in which glass plates are lifted by selecting plates for courses; the collective lifting mode in which glass are lifted only when all the courses for one glass plate row can be lifted; and the course-wise lifting mode in which only those glass plates for a specified course are lifted. The glass plates 113 lifted are sucked by the suction conveyor 111 and transported in the X-axis direction to a transfer car 115 via a brush conveyor 114.

Figure 4:
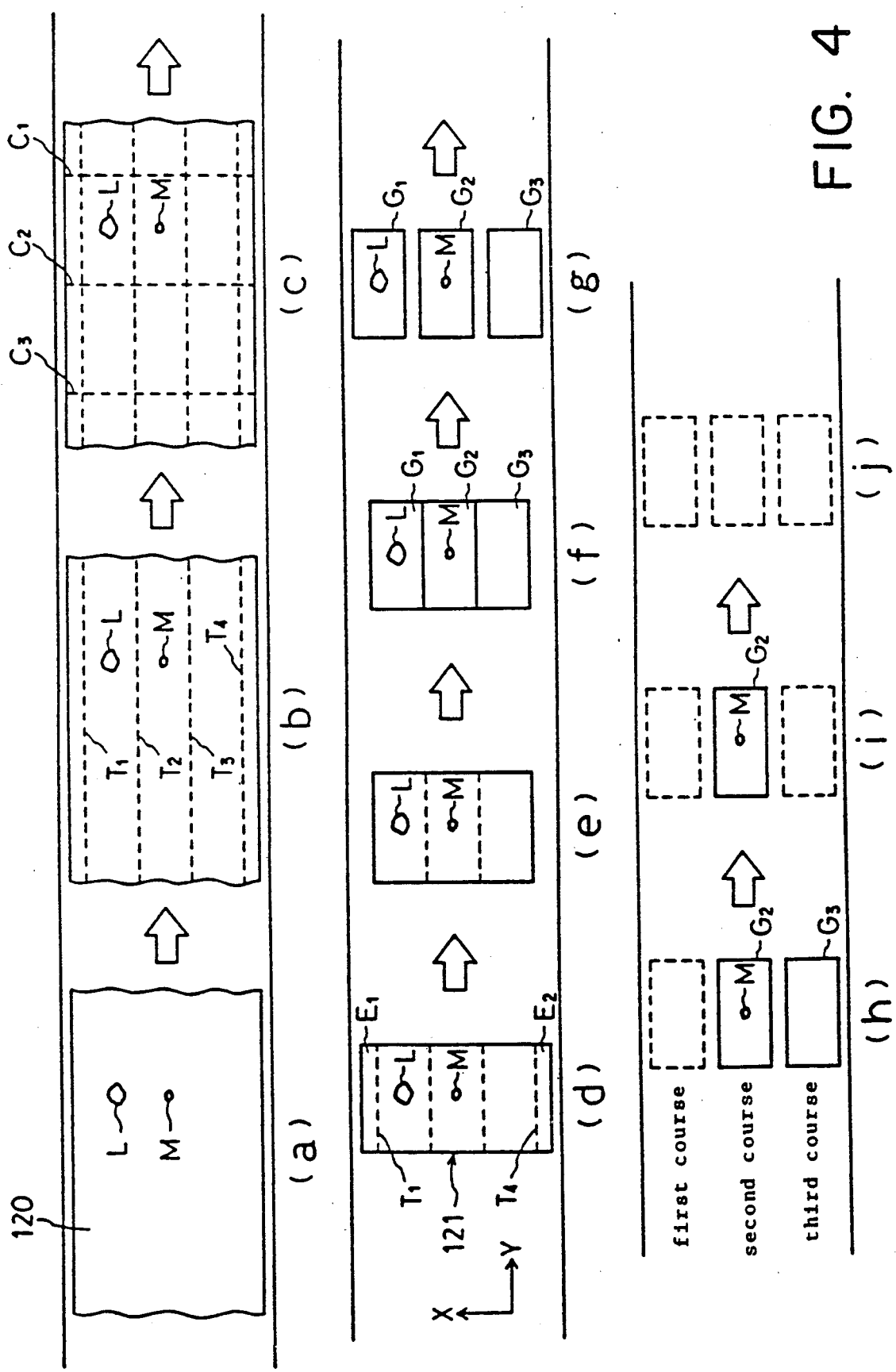
FIG. 4 is a diagram of assistance in explaining the operation required for sorting two grades of glass plates.

Now, the two-grade sorting process to sort high-grade and low-grade plates using the glass-plate sorting system having the above-mentioned construction will be described in the sequence of the process, referring to FIG. 4. FIG. 4 illustrates the sequence of the cutting and sorting operations of a glass strip travelling on the line conveyor 100.

PROCESS (a)

When the glass strip 120 pulled up from the furnace travels on the line conveyor 100 to the discriminating-type flaw detector 101, the detector 101 detects flaws existing in the glass strip 120, and transmits the flaw data information representing the types, sizes and locations of the flaws to the control unit 102. Now, assume that there exist a large-size flaw L and a medium-size flaw M in the glass strip 120, as shown in the figure.

PROCESS (b)

As the glass strip 120 arrives at the trimming-line marker 103, four trimming lines $T_1$, $T_2$, $T_3$ and $T_4$ are marked on the glass strip 120 in the Y-axis direction by the trimming-line marker 103.

PROCESS (c)

Then, cutting lines $C_1$, $C_2$, $C_3$, - - - are successively marked in the X-axis direction by the diagonal cutter 104.

PROCESS (d)

As the glass strip 120 marked with trimming and cutting lines arrives at the breaker 105, the breaker 105 breaks the glass strip 120 into glass-plate rows along the cutting lines. FIG. 4 shows a broken glass-plate row 121 between the cutting lines $C_1$ and $C_2$. It is assumed that the glass-plate row 121 has the large-size flaw L and the medium-size flaw M, mentioned above.

PROCESS (e)

The trimming cutter 106 cuts and removes trimmings $E_1$ and $E_2$, which are the edge parts of the glass-plate row 121, along the trimming lines $T_1$ and $T_4$.

PROCESS (f)

The trimmed glass-plate row 121 is slit into three glass plates $G_1$, $G_2$ and $G_3$ by the slitter 107, and the glass plates $G_1$, $G_2$ and $G_3$ are slightly separated apart in the X-axis direction.

PROCESS (g)

The three glass plates thus slit $G_1$, $G_2$ and $G_3$ are further separated apart in the X-axis direction by the separator 108 to direct to the first, second and third courses.

Since the control unit 102 keeps track of the locations of the flaws detected by the discriminating-type flaw detector 101 and controls the locations of the trimming lines marked by the trimming-line marker 103 and the cutting lines marked by diagonal cutter 104, the control unit 102 knows what sizes of the flaws exist at what locations in the glass plates separated apart by the separator 108. Thus, the control unit 102 identifies the glass plate having the medium-size flaw M as a high-grade-out, that is, a low-grade product, the glass plate having the large-size flaw L as a low-grade-out, that is, a defective plate being discarded, and the remaining as a high-grade product. In this way, the glass plates are sorted into high-grade, low-grade and defective products. In doing so, the control unit 102 knows that the glass plate $G_1$ has the large-size flaw L, the glass plate $G_2$ has the medium-size flaw M, and the glass plate $G_3$ has no flaws, and therefore determines the glass plate $G_3$ as a high-grade product, the glass plate $G_2$ as a low-grade product, and the glass plate $G_1$ as a defective product. Based on the judgement, the control unit 102 controls the eliminating/discarding unit and the sorter.

PROCESS(h)

As the glass plates $G_1$, $G_2$ and $G_3$ arrive at the eliminating/discarding unit 109, the control unit 102 lowers the discarding roll 90 for the first course, on which the defective plate $G_1$ travels, for removal from the line and disposal.

PROCESSES (i) and (j)

When the remaining low-grade product $G_2$ and the high-grade product $G_3$ on the second and third courses arrive at the sorting section having a plurality of sorters, the control unit 102 controls the sorters to sort the high-grade and the low-grade products. Now, assume that each sorter sorts high-grade or low-grade products for each course. That is, the sorter 110-1 sorts high-grade products for the first course, the sorter 110-2 sorts high-grade products for the second course, the sorter 110-3 sorts high-grade products for the third course, the sorter 110-4 sorts low-grade products for the first course, the sorter 110-5 sorts low-grade products for the second course, and the sorter 110-6 sorts low-grade products for the third course.

As a high-grade product $G_3$ on the third course arrives at the sorter 110-3, the control unit 102 controls the lifter 112 of the sorter 110-3 to selectively lift the high-grade product $G_3$. Similarly, as a low-grade product $G_2$ on the second course arrives at the sorter 110-5, the control unit 102 controls the lifter 112 of the sorter 110-5 to lift the low-grade product $G_2$.

As described above, the two-grade sorting process using the sorting system of this invention is capable of sorting high-grade and low-grade products simultaneously. Sorting the low-grade products that have heretofore been discarded in this way lead to increased yield in the manufacture of glass plates.

Next, the sorting process of automotive windshields using the sorting system shown in FIG. 1 will be described in the following.

Figure 5:
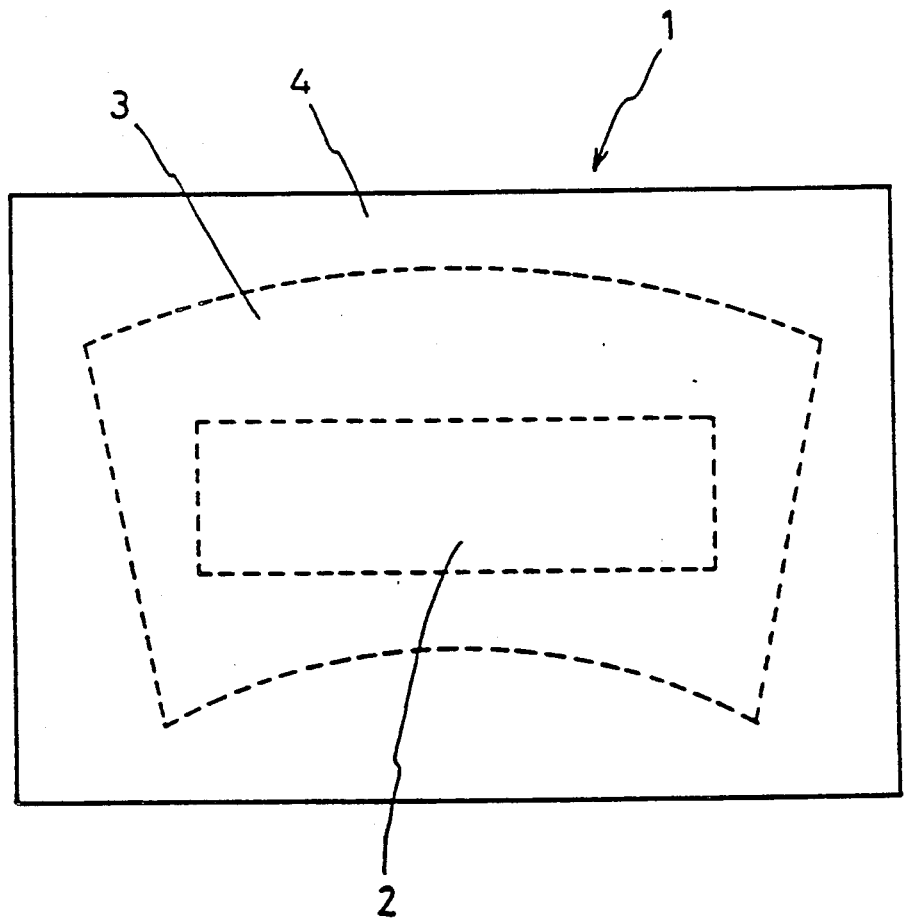
FIG. 5 is a diagram illustrating the see-through, peripheral and fringe areas of an automotive windshield assumed on a glass plate from which an automotive wind-shield is obtained.

As noted earlier, the quality of glass plates from which automotive windshields are obtained is such that the glass plates need not be free of flaws over the entire surface thereof. Although the see-through area 2, which is critical in terms of driver's visibility, of a glass plate 1 shown in FIG. 5 must be free of flaws, the peripheral area 3 around the see-through area 2 may have a certain degree of flaws. Moreover, the fringe area 4, which is eventually discarded, may have any types of flaws.

In the manufacture of automotive windshields, therefore, yield can be improved by sorting glass plates for windshields by detecting the sizes and locations of flaws in glass plates, and judging what size of flaws exist in the see-through area 2, peripheral area 3 and fringe area 4 assumed on the glass plate 1.

Figure 6A:
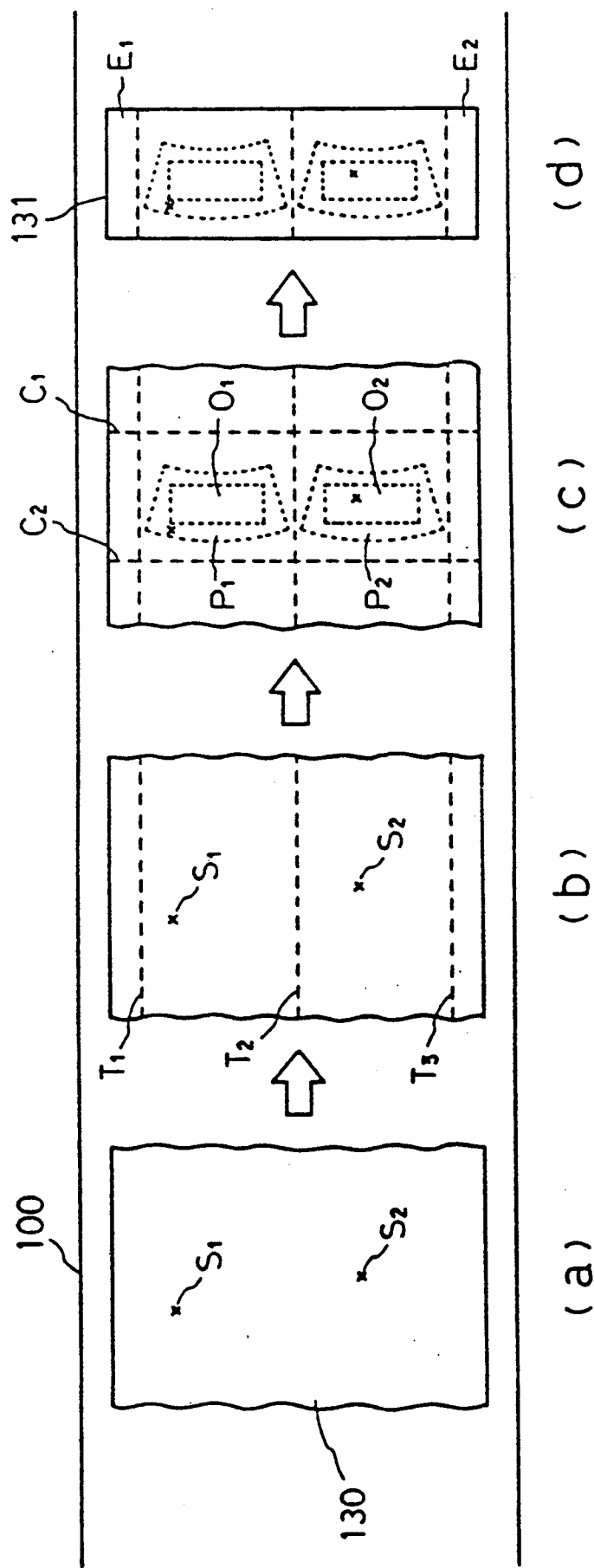
FIGS. 6A and 6B are diagrams of assistance in explaining the operation required for sorting automotive wind-shields.
Figure 6B:
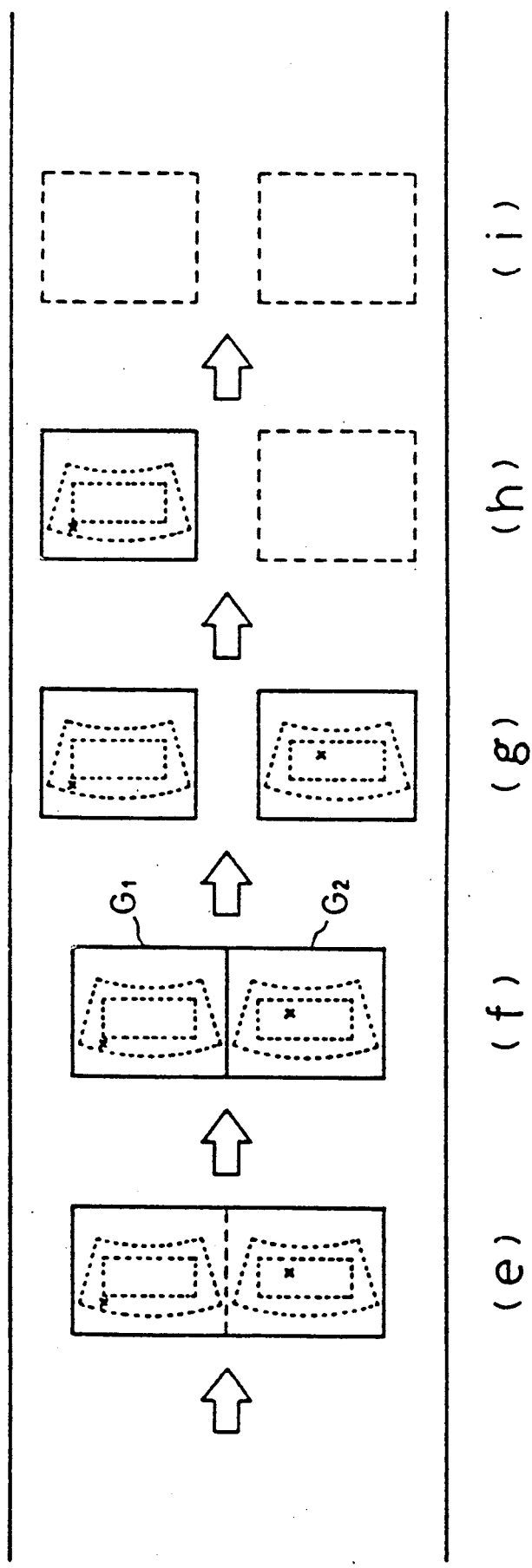

Now, the sorting process, using the sorting system shown in FIG. 1, of glass plates for automotive windshields whose see-through area is of a high grade having no flaws, and whose peripheral area is of a low grade where small flaws are permitted will be described in the order of production sequence, referring to FIGS. 6A and 6B. FIGS. 6A and 6B shows the cutting and sorting sequence of a glass strip on the line conveyor 100.

PROCESS (a)

As a glass strip 130 pulled up from the furnace travels on the line conveyor 100 to the discriminating-type flaw detector 101, the detector 101 detects a flaw existing in the glass strip 130, and transmits flaw data information representing the types, sizes and locations of the flaws to the control unit 102. Now assume that there exist two small flaws $S_1$ and $S_2$ in the glass strip 130, as shown in the figure.

PROCESS (b)

As the glass strip 130 arrives at the trimming-line marker 103, three trimming lines $T_1$, $T_2$ and $T_3$ are marked in the Y-axis direction by the trimming-line marker 103.

PROCESS (c)

Then, cutting lines $C_1$, $C_2$, - - - are successively marked by the diagonal cutter 104.

Since the control unit 102 keeps track of the locations of the flaws detected by the discriminating-type flaw detector 101 and controls the locations of the trimming lines marked by the trimming-line marker 103 and the cutting lines marked by the diagonal cutter 104, the control unit 102 knows what sizes of the flaws exist at what locations in the glass plates separated apart by the separator 108. Furthermore, the control unit 102 assumes see-through, peripheral and fringe areas on the glass plate, sets quality grades for the see-through and peripheral areas to judge the acceptability of the glass plate in accordance with the quality grade settings. In the process (c) shown in the figure, the control unit 102 assumes the see-through areas $O_1$ and $O_2$, the peripheral areas $P_1$ and $P_2$ on the glass plate being cut, and knows that one small flaw $S_1$ is present in the peripheral area $P_1$ and the other small flaw $S_2$ is present in the see-through area $O_2$. Thus, the control unit 102 determines the glass plate being cut having the small flaw $S_1$ as a good product, and the glass plate being cut having the small flaw $S_2$ as a no-good product. The control unit also controls the eliminating/discarding unit and the sorter, base on the judgement.

PROCESS (d)

As the glass strip 130 marked with trimming and cutting lines arrives at the breaker 105, the breaker 105 breaks the glass strip 130 into glass-plate rows along the cutting lines. FIG. 6A shows a broken glass-plate row 131 between the cutting lines $C_1$ and $C_2$.

PROCESS (e)

The trimming cutter 106 cuts and removes trimmings $E_1$ and $E_2$, which are the edge parts of the glass-plate row 131 along the trimming lines $T_1$ and $T_3$.

PROCESS (f)

The trimmed glass-plate row 131 is slit into two glass plates $G_1$ and $G_2$ by the slitter 107, and the glass plates $G_1$ and $G_2$ are slightly separated apart in the X-axis direction. As is evident from the above description, the glass plate $G_1$ is a good product, and the glass plate $G_2$ a no-good product.

PROCESS (g)

The two glass plates thus slit $G_1$ and $G_2$ are further separated apart in the X-axis direction by the separator 108 to direct to the first and second courses.

PROCESS (h)

As the glass plates $G_1$ and $G_2$ arrive at the eliminating/discarding unit 109, the control unit 102 lowers the discarding roll for the second course, on which the defective plate $G_2$ travels, for removal from the line and disposal.

PROCESS (i)

When the remaining low-grade product $G_1$ on the first course arrives at the sorting section, the control unit 102 controls the lifter of the sorter 110-1 to lift the good product $G_1$ and transport by the suction conveyor to the transfer car.

As described above, the sorting process of automotive windshields using the sorting system of this invention makes it possible to sort as a good product the glass plate $G_1$ that has heretofore been discarded, leading to increased yield in the manufacture of automotive windshields.

Although the above description concerns with the sorting of glass plates for automotive windshields into those of a high grade having no flaws in the see-through area and those of a low grade that allows small flaws in the peripheral area, establishing the criteria for high- and low-grades depends on the quality requirements for specific automotive windshields.

Next, the construction of the discriminating-type flaw detector 101 will be described in detail. As noted earlier, the present applicant had already developed a discriminating-type flaw detector and filed a patent application in Japan under the title of "A Discriminating-Type Flaw Detector For Light-Transmitting Plate Materials" on May 27, 1987 (Japanese Patent Application No. 62-128089). According to this Japanese Patent Application, flaws existing in a glass plate include bubbles formed by air bubbles remaining inside the glass plate, foreign matter remaining inside the glass plate, knots formed by almost molten foreign matter remaining inside the glass plate in a shape having a streaming tail, and drips formed by the metallic tin content of tin bath deposited on the glass plate surface. When such a flaw exists in a glass plate, projecting a light spot on the flaw products varied states of light, such as transmission, transmission and diffusion, reflection, and reflection and diffusion, depending on the type of the flaw. Eying this fact, the present applicant collected a large amount of data through various experiments to see how the state of transmission, transmission and diffusion, reflection, or reflection and diffusion would change according to the types of flaws in a glass plate. Part of the analysis results of the data will be described in the following.

Figure 7:
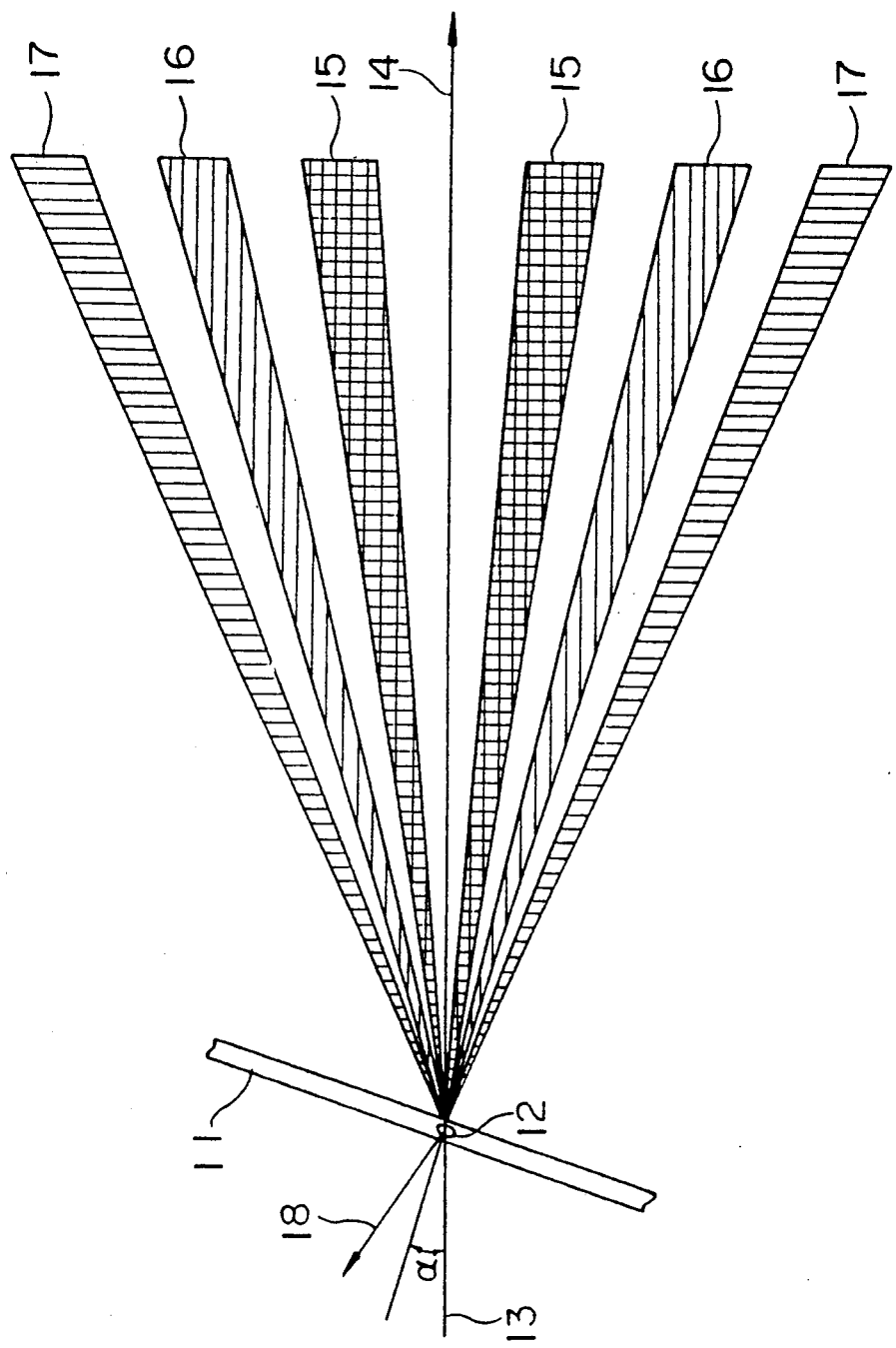
FIG. 7 is a diagram illustrating transmitted light and transmitted and diffused light.

As shown in FIG. 7, when a light beam 13 is projected on a flaw 12 existing in a transparent glass plate 11 at a predetermined incident angle $\alpha$ with respect to the normal, a knot, foreign matter, or an air bubble produces a transmitted and diffused light beam. Particularly, a knot will produce the most paraxial transmitted and diffused light 15 that is closest to the optical axis of the transmitted light 14, a foreign material would produce paraxial transmitted and diffused light 16 which is close to the optical axis of the transmitted light 14, and a bubble would produce the least paraxial transmitted and diffused light 17 which is away from the optical axis of the transmitted light 14. All the bubble, foreign material, knot and drip reduce the amount of transmitted light 14, while the drip increases the amount of reflected light 18.

Consequently, if different light receptors each of which can detect transmitted light, the most paraxial transmitted and diffused light, paraxial transmitted and diffused light, the least paraxial transmitted and diffused light, and reflected light are provided to detect changes in the amounts of transmitted light and reflected light, and the presence/absence of the most paraxial transmitted and diffused light, paraxial transmitted and diffused light, and the least paraxial transmitted and diffused light, the types of flaws can be discriminated.

The above discussion is summarized in Table 1. In the table, a mark ○ denotes the ability of discriminating the types of a flaw.

TABLE 1

| Light Flaw | Transmitted light | Most paraxial transmitted/ diffused light | Paraxial transmitted/ diffused light | Least paraxial transmitted/ diffused light | Reflected light |
|---|---|---|---|---|---|
| Bubble | O | | | O | |
| Foreign matter | O | | O | | |
| Knot | O | O | | | |
| Drip | O | | | | O |

The present applicant found that the amount of light detected by each light receptor is proportional to the size of a flaw. Consequently, the size of a flaw can be determined by detecting the amount of light detected by each light receptor.

Although what has been described above is a part of the knowledge obtained by the present applicant, it is also known that there is a certain relationship between the type of a flaw and the state of reflected and diffused light.

Based on the above consideration, the discriminating type flaw detector 101 has a plurality of light receptors each of which detects at least more than two types of light beams among transmitted light, the most paraxial transmitted and diffused light, paraxial transmitted and diffused light, the least paraxial transmitted and diffused light, reflected light, and reflected and diffused light to convert the light beams received from the light receptors to electrical signals, produce flaw data containing the information representing the types and sizes of flaws by processing the electrical signals obtained, prepare a flaw pattern consisting of bit patterns corresponding to the flaws on a glass strip by further processing the flaw data, and compare the flaw pattern thus obtained with a prestored flaw discriminating pattern table to judge the types and sizes of flaws.

The discriminating-type flaw detector 101 is also designed to detect the location of a flow in a glass strip. Thus, the discriminating-type flaw detector 101 eventually can discriminate and detect the types, sizes and locations of flaws.

Figure 8:
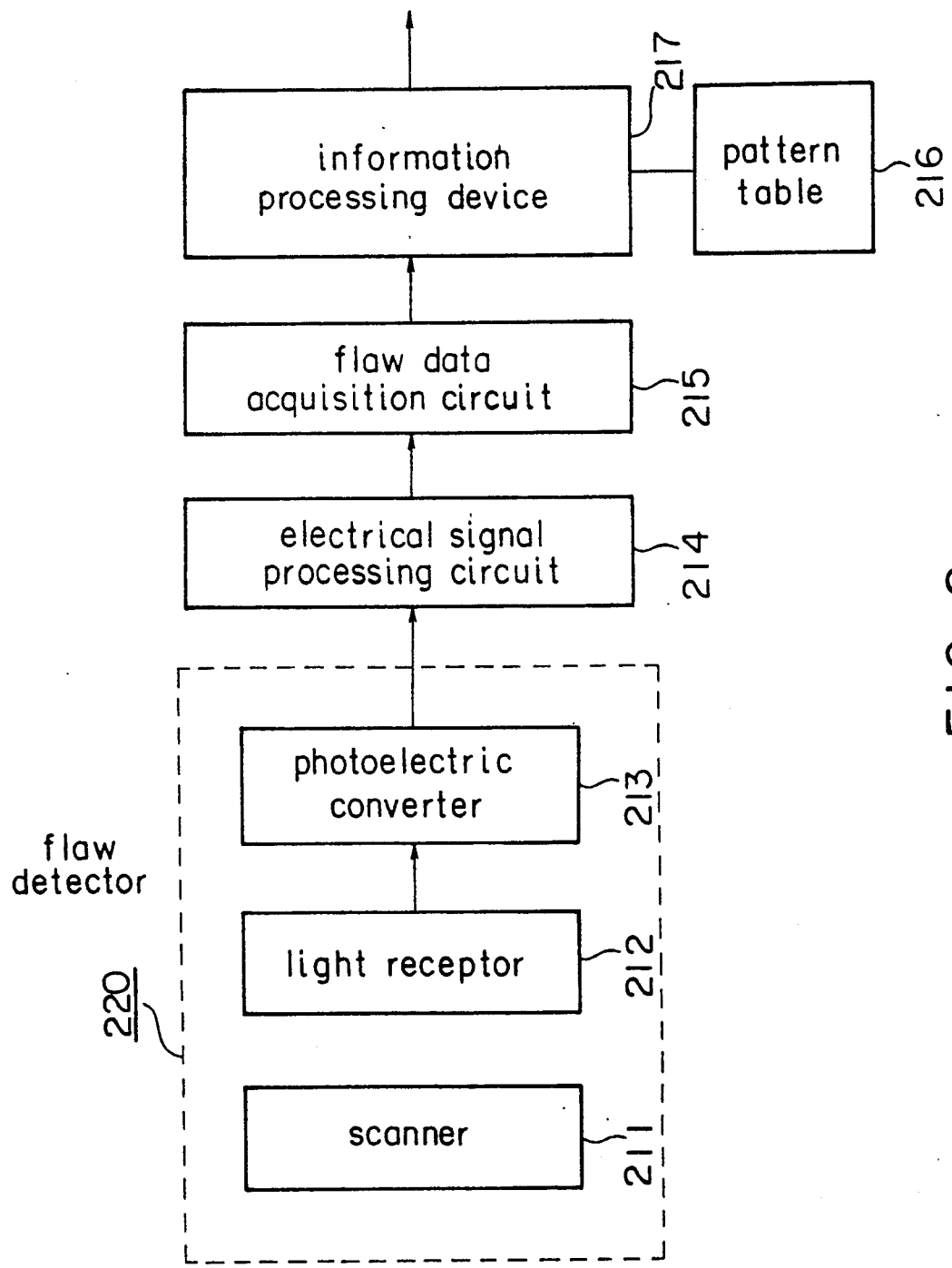
FIG. 8 is a block diagram illustrating the basic construction of a discriminating-type flaw detector.

FIG. 8 is a block diagram outlining the overall construction of the discriminating-type flaw detector 101. The discriminating-type flaw detector comprises a scanner 211 which scans a travelling glass strip with a laser spot formed by reflecting a laser beam with a rotating multiplanar mirror; a plularity of light receptors 212 for receiving the transmitted light, transmitted and diffused light and reflected light of the laser spot as the laser spot scans flaws in the travelling glass strip; a photoelectric converter 213 which converts the light received by each light receptor to an electrical signal; an electrical signal processing circuit 214 which genarates flaw data containing infromation on the types and sizes of flaws by processing the electrical signal from the photoelectric converter 213; a flaw data acquisition circuit 215 which collects the flaw data generated by the electrical signal processing circuit 214, a signal processing clock and a line synchronization signal, forms from the flaw data a flaw pattern consisting of bit trains representing the types and sizes of flaws existing in the travelling glass strip, and adds information on the locations of flaws to the flaw pattern; and an information processing device 217 which receives the flaw pattern from the flaw data acquisition curcuit 215 and te informations on the locations of flaws, discriminates the types and sizes of flaws by comparing the flaw pattern with a prestored flaw discriminating pattern table 216, and feeds the discrimination results and the information on the locations of flaws to the control unit 102.

In the following, description will be made on the flaw detector 220 comprising the scanner 211, the light receptor 212 and the photoelectric converter 213.

Figure 9:
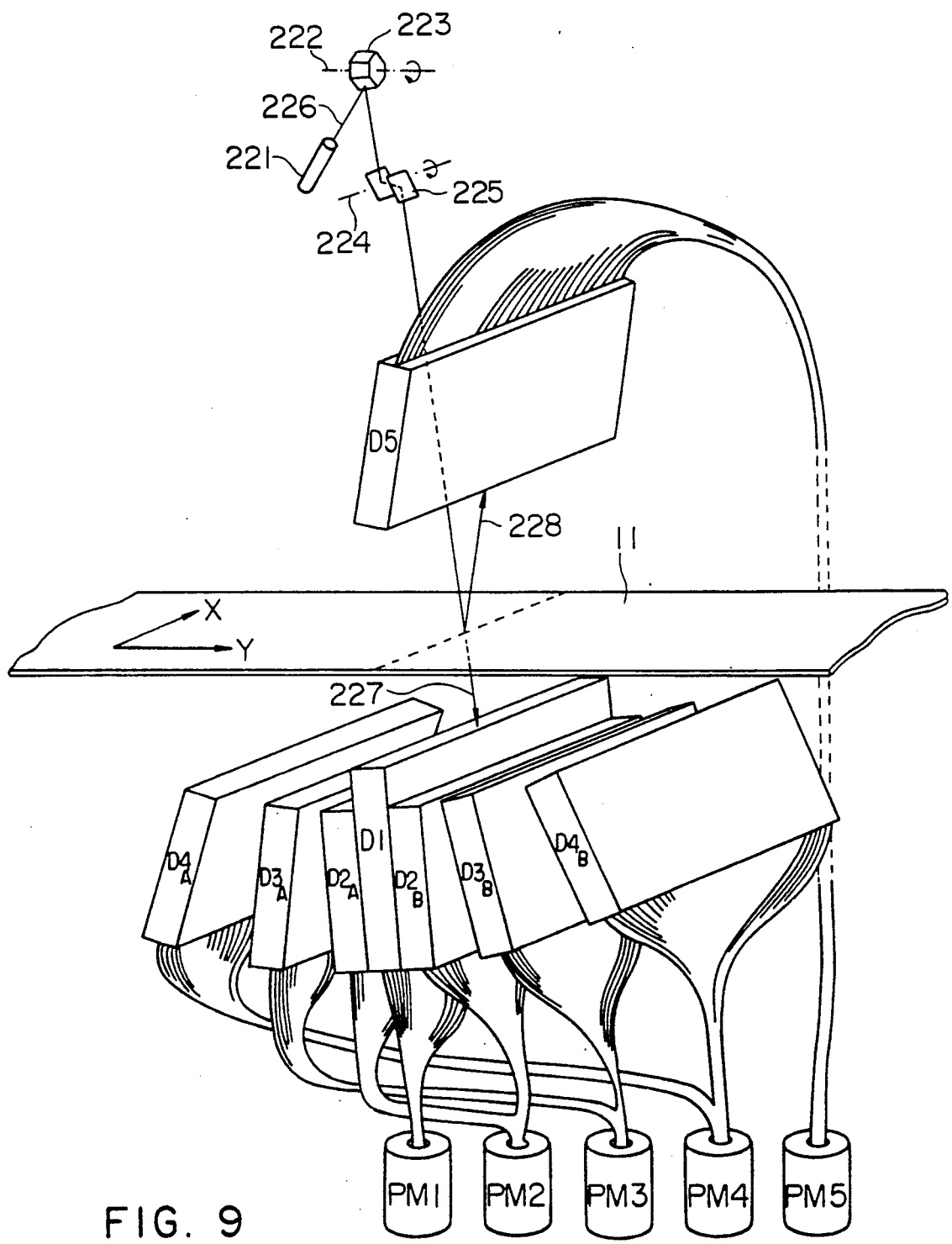
FIG. 9 is a perspective view of a flaw detector.

FIG. 9 is a perspective view of the flaw detector 220, with the light receptor shown in an exaggerated form for clarity.

Figure 10:
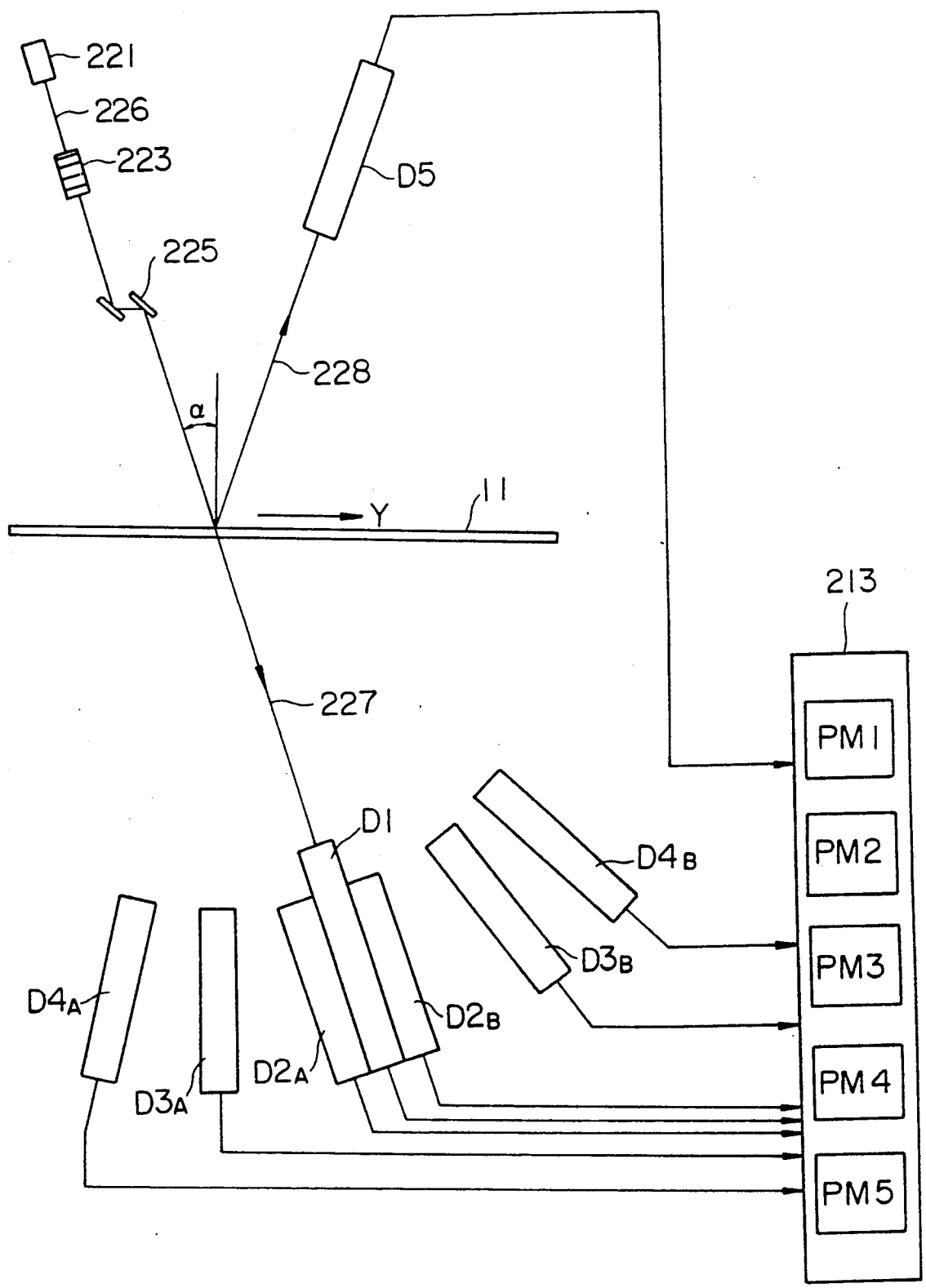
FIG. 10 is a side elevation of the flaw detector.

FIG. 10 is an outline drawing of the flaw detector viewed in the direction normal to the travelling direction of a glass strip. Like parts are indicated by like numerals in FIGS. 9 and 10.

The scanner 211 has a laser light source 221 emitting laser light, a rotating multiplanar mirror 223 rotating at high speed around an axis 222 parallel with the travelling direction of a glass strip 11 (hereinafter referred to as the Y-axis direction), upon which a laser beam 226 from the laser light source 221 falls, and a parallel-mirror assembly 225 for thickness correction which can change the angular location thereof by rotating around an axis 224 paralles with the across-the-width direction of the glass strip 11 (hereinafter referred to as the X-axis direction), that is, in the direction normal to the Y-axis direction. The location of the laser light source 221 is shown in FIG. 10 in a different way from the actual location thereof for clarity.

The scanner having the aforementioned construction is installed above the travelling glass strip 11.

The laser beam 226 emitted from the laser light source 221 falls on the rotating multiplanar mirror 223 that rotates at high speed. The laser beam 226 is diverted by the rotating multiplanar mirror 223 toward the X-axis direction, reflected by the parallel-mirror assembly 225 and then falls on the travelling glass strip 11 to scan the glass strip in the X-axis direction. Every time the reflecting surface of the rotating multiplanar mirror 223 is changed as the mirror 223 rotates, the laser beam 226 repeatedly scans the glass strip 11. Since the glass strip 11 travels in the Y-axis direction, the entire surface of the glass strip 11 is scanned by the laser beam.

As shown in FIG. 10, the laser beam 226 arrives at the glass strip 11 at an incident angle $\alpha$ with respect to a normal to the glass strip surface. This is to prevent interference of the light reflected by the rear surface of the glass strip 11, then reflected again by the front surface and leaving the rear surface with the transmitted light 227. The value of $\alpha$ should preferably be more than 13°.

Next, the arrangement and construction of the light receptor will be described. On the opposite side to the side on which the scanner is installed, or below the glass strip 11, provided are a light receptor D1 for detecting the transmitted light 227, two light receptors $D2_A$ and $D2_B$ for detecting the most paraxial transmitted and diffused light, two light receptors $D3_A$ and $D3_B$ for detecting the paraxial transmitted and diffused light, and two light receptors $D4_A$ and $D4_B$ for detecting the least paraxial transmitted and diffused light. Above the glass strip 11, provided is a light receptor D5 for detecting the reflected light 228.

These multiple light receptors have essentially the same construction, each equipped with a slender linear light-receiving surface extending in the X-axis direction. In the following, the construction of a light receptor D1 will be described as a typical example.

Figure 11:
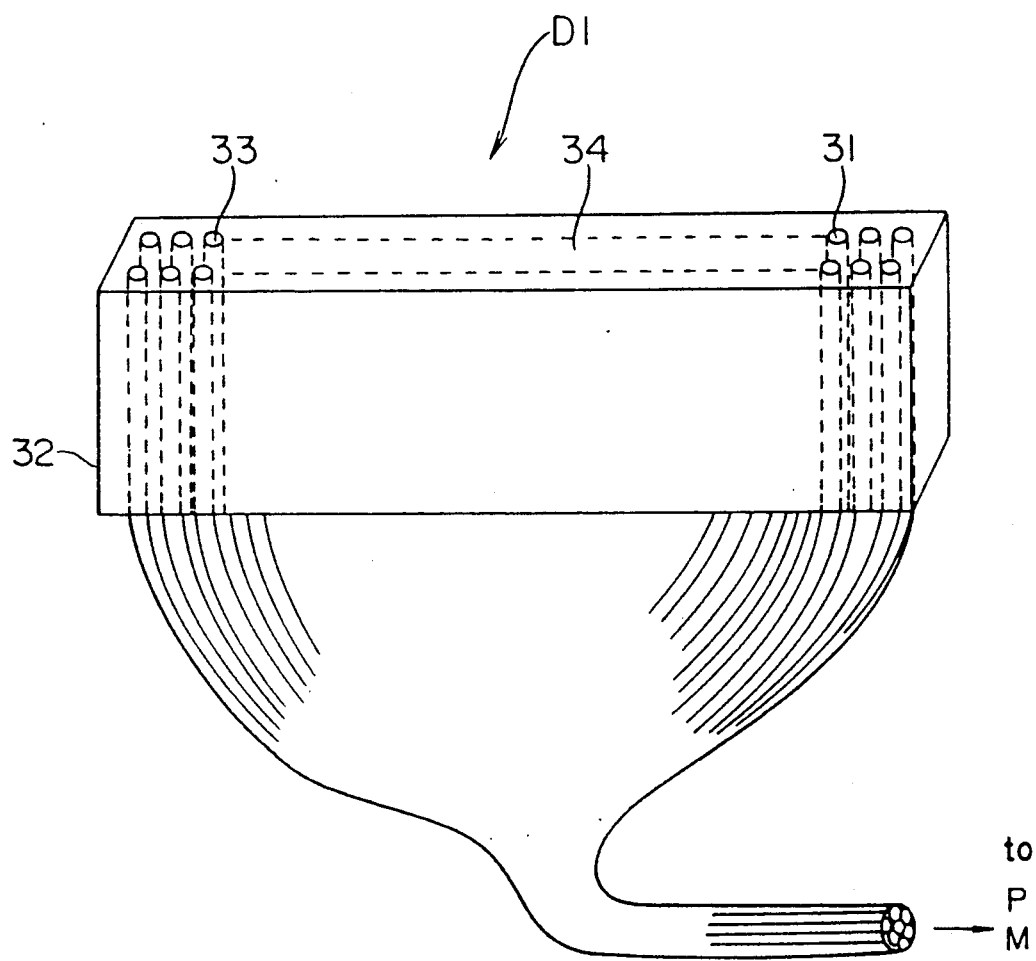
FIG. 11 is a perspective view of a light receptor.

FIG. 11 is a perspective view of the light receptor D1. The light receptor D1 consists of multiple optical fibers 31 which are arranged at one end thereof in two rows and held in place by casting filler resin to form the light receptor proper 32. The end faces 33 of the arranged multiple optical fibers 31 are assembled into a slender linear light-receiving surface 34. The other ends of the optical fibers 31 are bundled and connected to photomultiplier tubes, which will be described later.

Although the optical fibers are arranged in two rows in the above example, the mode of optical fiber arrangement is not limited to this arrangement.

When installing the light receptors D1, $D2_A$, $D2_B$, $D3_A$, $D3_B$, $D4_A$ and $D4_B$ of the above-mentioned construction for detecting transmitted light and transmitted and diffused light, each light receptor is installed in such a manner that the light-receiving surface thereof is located with the effective light-receiving angles thereof. A typical relationship between the light receptor and the effective light-receiving angle thereof is shown in Table 2.

TABLE 2

| Light receptor | Effective light-receiving angle |
|---|---|
| D1 | $0° - \pm 0.43°$ |
| $D2_A, D2_B$ | $\pm 0.43° - \pm 0.71°$ |
| $D3_A, D3_B$ | $\pm 1.59° - \pm 2.05°$ |
| $D4_A, D4_B$ | $\pm 8.13° - \pm 9.46°$ |

Figure 12:
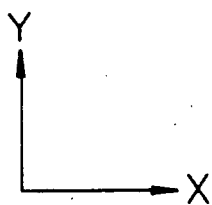
FIG. 12 is a plan view of the light-receiving surfaces of a plurality of light receptors for transmitted light and transmitted and diffused light.
Figure 12:
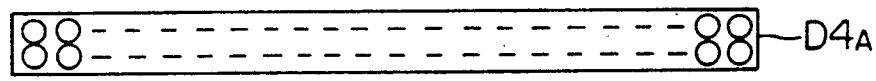
Figure 12:
Figure 12:
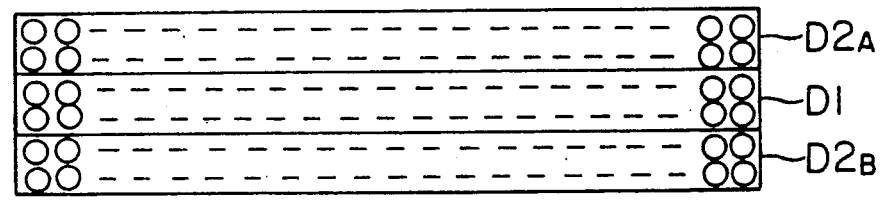
Figure 12:
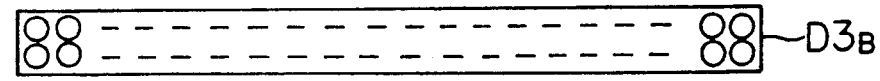
Figure 12:

FIG. 12 shows the light receptors D1, $D2_A$, $D2_B$, $D3_A$, $D3_B$, $D4_A$ and $D4_B$ arranged in such a fashion that the light-receiving surfaces thereof are located within the effective light-receiving angle shown in the table above, viewed from the light-receiving surfaces. The longitudinal direction of the light-receiving surface of each light receptor is parallel to the X-axis direction. Two light receptors each for detecting the most paraxial transmitted and diffused light, the paraxial transmitted and diffused light, and the least paraxial transmitted and diffused light are used in order to prevent these transmitted and diffused light beams from being overlooked.

As shown in FIGS. 9 and 10, the location of the light-receiving surface of the light receptor D1 for the transmitted light is shifted with respect to the optical axis from the location of the light-receiving face of the adjoining light receptors $D2_A$ and $D2_B$ for the most paraxial transmitted and diffused light to prevent the transmitted light from being further diffused by the light-receiving surface of the light receptor D1 and entering the light receptors $D2_A$ and $D2_B$.

The light receptor D5 for detecting the reflected light may be formed by optical fibers, as described above, but a diffuser box may be used to collect the light, which is then fed to a photomultiplier tube, which will be described later, via optical fibers. In this case, it is recommended that a mask having a slit should be provided on the light-receiving face of the diffuser box to shield unwanted light.

The flaw detector 220 (FIG. 8) has five photomultiplier tubes PM1, PM2, PM3, PM4 and PM5 as photoelectric converters, as shown in FIG. 9, with the photomultiplier tube PM1 being connected to the other ends of the optical fibers of the light receptor D1, the photomultiplier tube PM2 being connected to the other ends of the optical fibers of the light receptor $D2_A$ and $D2_B$, the photomultiplier tube PM3 being connected to the other ends of the optical fibers of the light receptors $D3_A$ and $D3_B$, the photomultiplier tube PM4 being connected to the other ends of the optical fibers of the light receptors $D4_A$ and $D4_B$, and the photomultiplier tube PM5 being connected to the other ends of the optical fibers of the light receptor D5. Each photomultiplier tube converts received light into electrical signals.

Though now shown, an optical fiber for forming a start pulse are provided between the rotating multiplanar mirror 223 and the parallel-mirror assembly 225 of the scanner, and a photoelectric converter for converting the light received by these optical fibers into an electrical signal and a pulse shaper for forming a start pulse ST are provided. The start pulse ST is used as a start-to-scan signal in the flaw data acquisition circuit 215, which will be described later.

When the thickness of the glass strip 11 changes, the light paths of the transmitted light, the transmitted and diffused light and the reflected light could be changed, with the result that the light beams fail to fall upon the light-receiving surfaces of the light receptors. In such a case, the light paths of the transmitted light and the transmitted and diffused light, for example, can be kept unchanged by changing the light path of the incident light on the glass strip by turning the parallel-mirror assembly 225. When the parallel-mirror assembly 225 is adjusted to keep the light paths of the transmitted light and the transmitted and diffused light unchanged, the light path of the reflected light could be changed. This can be corrected by moving the light receptor D5 or the mask of the diffuser box if the light receptor D5 has such a diffuser box.

Now, the operation of the flaw detector 220 having the above-mentioned construction will be described for the case where a laser beam scans a flaw existing in the glass strip 11.

When the laser beam falls upon a flaw present in a glass strip, the amounts of the transmitted light and the reflected light change in accordance with the type of flaw (foreign matter, bubble, knot, drip), and at the same time, the transmitted and diffused light is generated.

In the case of a knot, for example, when the incident laser beam falls upon the knot, the amount of the transmitted light changes, and at the same time, the most paraxial transmitted and diffused light is generated. The change in the amount of the transmitted light is detected by the light receptor D1, fed to the photomultiplier tube PM1 and converted into an electrical signal. The most paraxial transmitted and diffused light, on the other hand, falls on the light-receiving faces of the light receptors $D2_A$ and $D2_B$. The most paraxial received transmitted and diffused light is fed to the photomultiplier tube PM2 and converted to an electrical signal.

Similarly, if the flaw is foreign matter, as the incident laser beam falls on the foreign matter, the amount of the transmitted light changes, and at the same time, the paraxial transmitted and diffused light is generated. The transmitted and diffused light is received by the light receptors $D3_A$ and $D3_B$, fed to the photomultiplier tube PM3 and converted to and electrical signal.

Similarly, if the flaw is a bubble, as the incident laser beam falls on the bubble, the amount of the transmitted light changes, and at the same time, the least paraxial transmitted and diffused light is generated. The least paraxial transmitted and diffused light is received by the light receptors $D4_A$ and $D4_B$, fed to photomultiplier tube PM4 and converted to an electrical signal.

Similarly, in the case of a drip, when the incident laser beam arrives at the drip, the amount of the transmitted light changes, and at the same time, the amount of the reflected light also changes. The change in the reflected light is detected by the light receptor D5, fed to the photomultiplier tube PM5 and converted to an electrical signal.

In this way, the changes in the amounts of the transmitted light and the reflected light caused by the flaw in the glass strip, and the most paraxial transmitted and diffused light, the paraxial transmitted and diffused light and the least paraxial transmitted and diffused light are sent from the flaw detector 220 to the electrical signal processing circuit 214 (FIG. 8) in the form of electrical signals.

Next, the construction of the electrical signal processing circuit 214 which generates flaw data containing information on the types and sizes of flaws by processing the electrical signals fed from the photomultiplier tubes PM1, PM2, PM3, PM4 and PM5 of the flaw detector will be described in the following.

Figure 13:
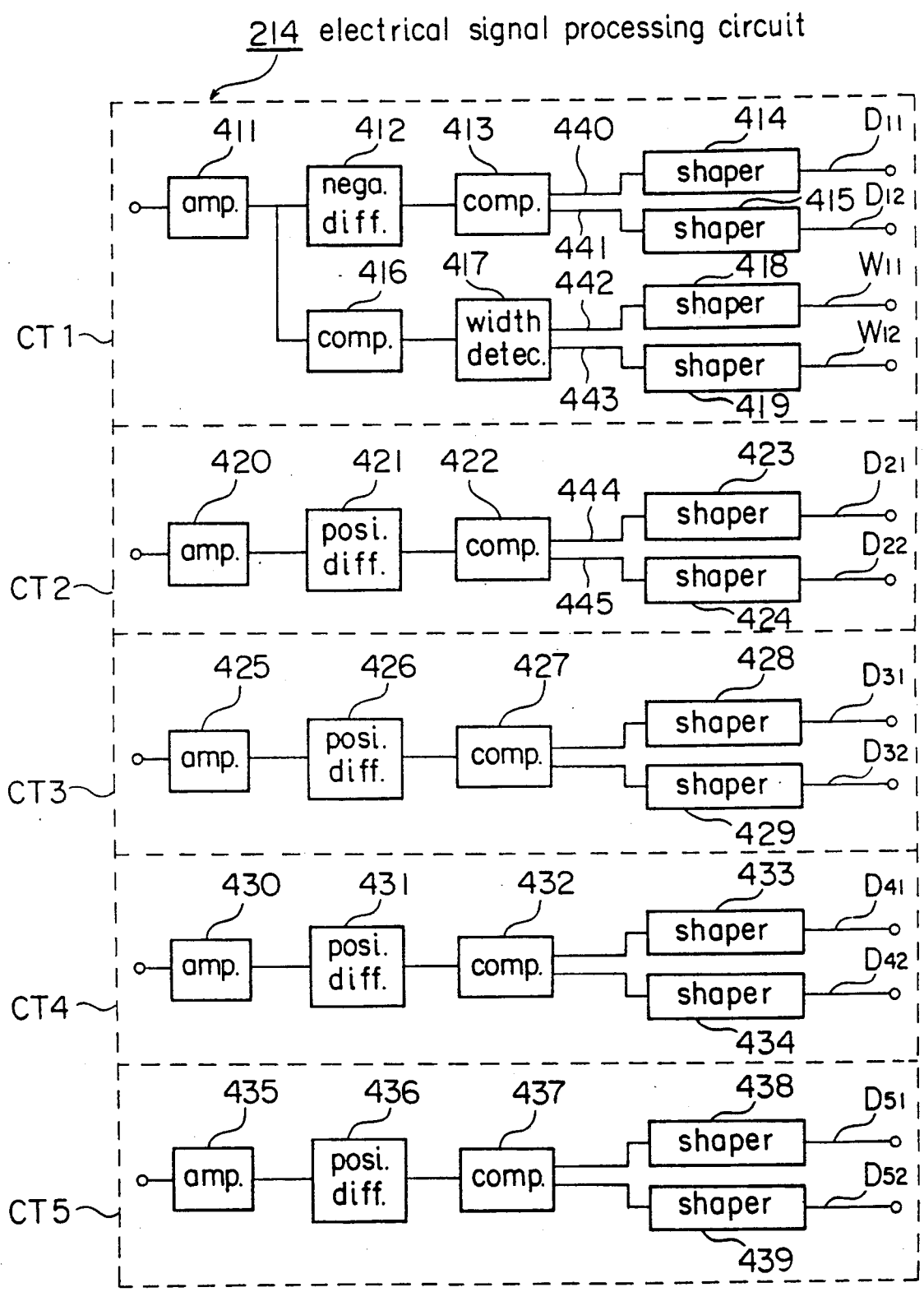
FIG. 13 is a block diagram of an electrical signal processing circuit.

FIG. 13 shows an example of the electrifcal signal processing circuit. The electrical signal processing circuit comprises flaw data generating portions CT1, CT2, CT3, CT4 and CT5 for generating flaw data by processing the electrical signals from the photomultiplier tubes PM1, PM2, PM3, PM4 and PM5.

The flaw data generating portion CT1 consists of an amplifier 411 for amplifying the electrical signal from the photomultiplier tube PM1, a negative differentiator 412 for differentiating the fall of the signal from the amplifier 411, a comparator 413 for comparing the level of the signal from the negative differentiator 412 with two detection levels, pulse shapers 414 and 415 for pulse-shaping the two signals output by the comparator 413, respectively, a comparator 416 for comparing the signal from the amplifier 411 with a detection level, a width detector 417 for comparing the width of the signal from the comparator 416 with two width judgement levels, and pulse shapers 418 and 419 for pulse-shaping the two signals output by the width detector 417.

The flaw data generating portion CT2 consists of an amplifier 420 for amplifying the electrical signal from the photomultiplier tube PM2, a positive differentiator 421 for differentiating the rise of the signal from the amplifier 420, a comparator 422 for comparing the level of the signal from the positive differentiator 421 with two detection levels, and pulse shapers 423 and 424 for pulse-shaping the two signals output by the comparator 422, respectively.

As the flaw data generating portions CT3, CT4 and CT5 have the same construction as the flaw data generating portion CT2, description has been omitted by giving only reference numerals to the elements thereof.

Next, the operation of the electrical signal processing circuit 214 will be described, referring to FIGS. 14A, 14B, 14C, 14D, 15A, 15B, 15C, 16A, 16B and 16C.

To begin with, the operation of the flaw data generating portion CT1 will be described. The flaw data generating portion CT1 generates flaw data containing information on the types and sizes of flaws from the electrical singal formed by the photomultiplier tube PM1 by converting the transmitted light detected by the light receptor D1.

Figure 14A:
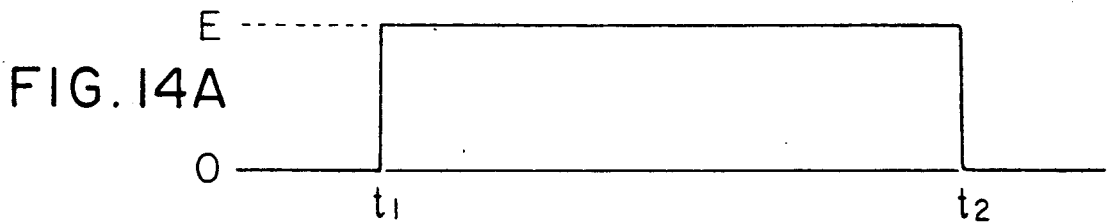
FIGS. 14A, 14B, 14C, 14D, 15A, 15B, 15C, 16A, 16B and 16C are waveform diagrams of assistance in explaining the operation of the electrical signal processing circuit.

The amplifier 411 amplifies the electrical signal sent from the photomultiplier tube PM1. FIG. 14A shows the waveform of the output voltage of the amplifier 411 when the laser beam of the flaw detector performs one scan on a glass strip having no flaws in the X-axis direction. The waveform indicates that the transmitted light is received by the light receptor D1 during one scan from time $t_1$ to time $t_2$, and the output level is E volts. In this way, the light receptor D1 receives transmitted light at all times during one scan.

Figure 14B:
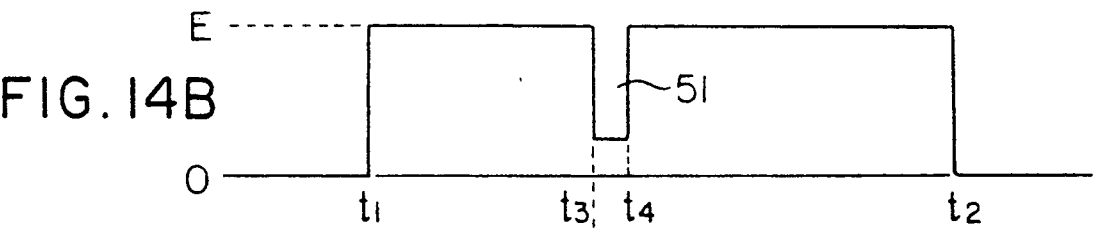
Figure 14C:
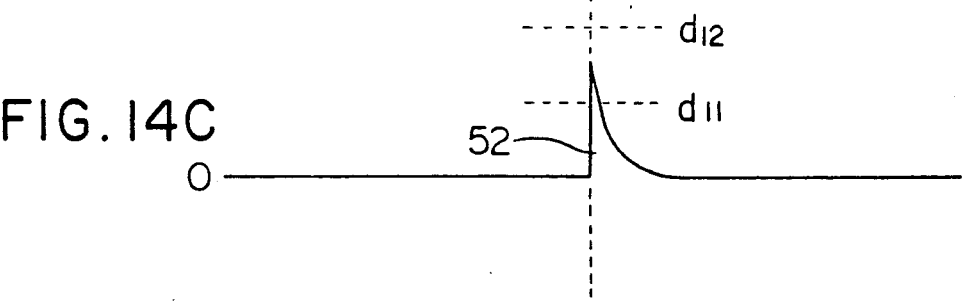

When a flaw is present in a glass strip, as a laser beam falls upon the flaw, the amount of the transmitted light is reduced, generating a fall pulse 51 in the output waveform as shown in FIG. 14B. In the figure, the fall pulse is shown in an exaggerated form for convenience of explanation, and it is assumed that the pulse falls at time $t_3$ and rises at time $t_4$. The fall level of the fall pulse 51 is proportional to the size of the flaw; the larger the size of flaw the larger becomes the width (from time $t_3$ to time $t_4$) of the fall pulse.

The negative differentiator 412 negatively differentiates the output of the amplifier 411 and outputs a differentiated pulse 52 which rises at the fall time $t_3$ of the fall pulse 51. The magnitude of the differentiated pulse is proportional to the fall level of the fall pulse 51.

The differentiated pulse 52 from the negative differentiator 412 is input to the comparator 413. The comparator 413 has two detection levels $d_{11}$ and $d_{12}$ ($d_{11} > d_{12}$), as shown by the output waveforms in FIG. 14C, with which the rise level of the input differentiated pulse 52 is compared.

Figure 14D:
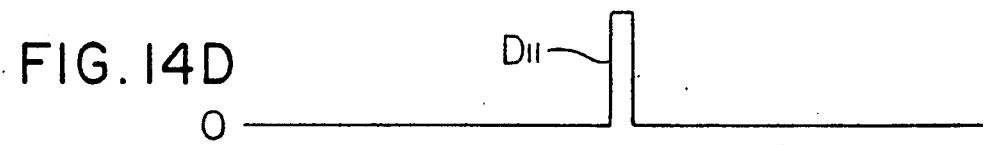

If the fall level of the input differentiated pulse is higher than the detection level $d_{11}$, the comparator 413 outputs a pulse from the first output terminal 440 thereof, and if the fall level of the input differentiated pulse is higher than the detection level $d_{12}$, the comparator 413 then outputs a pulse from the second output terminal 441 thereof. These pulses are shaped in the pulse shapers 414 and 415, and output as flaw date $D_{11}$ and $D_{12}$. In the case of the differenciated pulse 52 shown in FIG. 14C, as the fall level thereof is higher than the detection level $d_{11}$ and lower than the detection level $d_{12}$, flaw data $D_{11}$ shown in FIG. 14D is output. The difference between the flaw data $D_{11}$ and $D_{12}$ as discussed above represents the size of a flaw.

The electrical signal from the amplifier 411 is input to the comparator 416 and then to the width detector 417 for width judgement processing. This width judgement processing is carried out to produce flaw data containing information on the sizes of flaws, which is used for judgement in the glass-plate sorting system.

Figure 15A:
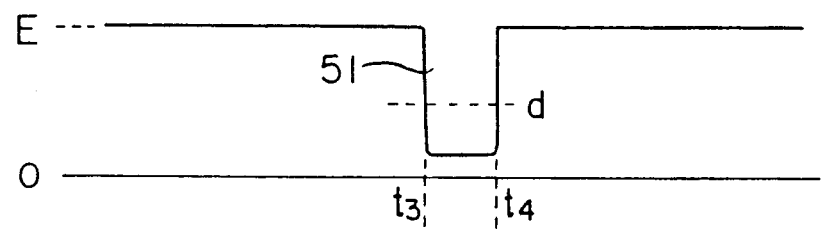
Figure 15B:
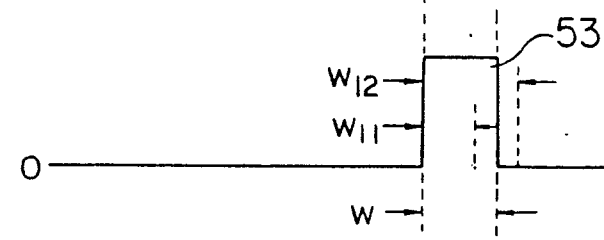
Figure 15C:
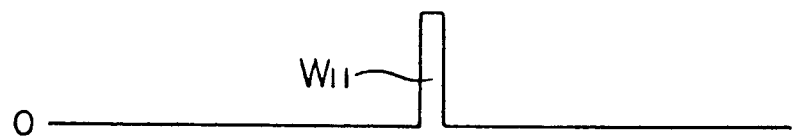

Now, this width judgement processing will be described, referring to FIGS. 15A, 15B and 15C showing waveforms. The waveform shown in FIG. 15A is the portion of the fall pulse 51 in the waveform shown in FIG. 14B, which is shown by expanding the time axis. The comparator 416 has a detection level d, and therefore if the fall level of the fall pulse 51 exceeds the detection level d, the comparator 416 outputs a pulse 53 having a width equal to the width w (from time $t_3$ to time $t_4$) when the fall pulse 51 is sliced with the detection level d.

The width detector 417 has two width judgement levels $w_{11}$ and $w_{12}$ ($w_{11} < w_{12}$), and compares the width w of the input pulse 53 with these judgement levels. The width detector 417 outputs a pulse from the first output terminal 442 thereof when the width w is larger than the judgement level $w_{11}$, and output a pulse from the second output terminal 443 when the width w is larger than the judgement level $w_{12}$. These pulses are shaped in the pulse shapers 418 and 419, and output as flaw data $W_{11}$ and $W_{12}$. In the case of the pulse 53 shown in FIG. 15B, the width w is larger than the judgement level $w_{11}$ and smaller than the judgement level $w_{12}$, so flaw data $W_{11}$ as shown in FIG. 15C is output.

The difference between the flaw data $W_{11}$ and $W_{12}$ as discussed above represents the size of a flaw. These flaw data $W_{11}$ and $W_{12}$ are used as judgement data for sorting glass plates, particularly of lower grades in the glass-plate sorting system.

Figure 16A:
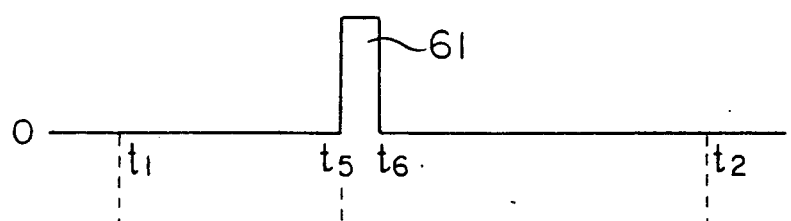
Figure 16B:
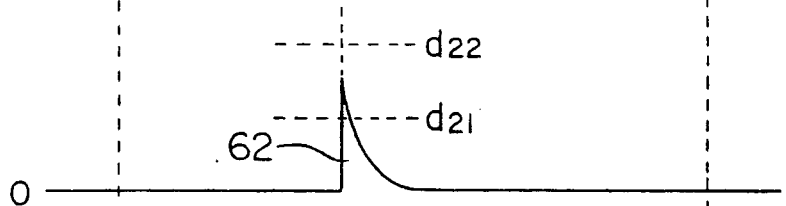
Figure 16C:
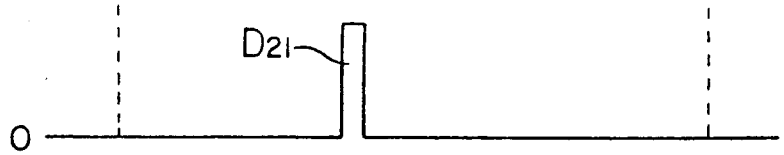

Next, the operation of the flaw data generating portion CT2 will be described, referring to FIG. 16A, 16B and 16C showing waveforms. The flaw data generating portion CT2 produces flaw data containing information on the types and sizes of flaws from the electrical signals produced by converting the most paraxial transmitted and diffused light detected by the light receptors $D2_A$ and $D2_B$ with the photomultiplier tube PM2. Electrical signals are fed from the photomultiplier tube PM2 only when a flaw (knot) is scanned by the laser beam. FIG. 16A shows the waveform of an electrical signal generated by the amplifier 420 when the knot is scanned. A rise pulse 61 is generated from time $t_5$ to time $t_6$. In the positive differentiator 421, the output of the amplifier 420 is positively differentiated, and a differentiated pulse 62 which rises at the rise time $t_5$ of the rise pulse 61 is output, as shown in FIG. 16B. The level of this differentiated pulse is proportional to the rise level of the rise pulse 61.

The differentiated pulse 62 from the positive differentiator 421 is input to the comparator 422. The comparator 422 has two detection levels $d_{21}$ and $d_{22}$ ($d_{21} < d_{22}$), as shown in the waveform shown in FIG. 16B, and compares the rise level of the input differentiated pulse 62 with these detection levels.

The comparator 422 outputs a pulse from the first output terminal 444 thereof if the rise level of the input differentiated pulse 62 is higher than the detection level $d_{21}$, and outputs a pulse from the second output terminal 445 if the rise level of the input differentiated pulse 62 is higher than the detection level $d_{22}$. These pulses are shaped in the pulse shapers 423 and 424, and output as flaw data $D_{21}$ and $D_{22}$. In the case of the differentiated pulse 62 shown in FIG. 16B, as the rise level thereof is higher than the detection level $d_{21}$ and lower than $d_{22}$, flaw data $D_{21}$ as shown in FIG. 16C is output. The difference between the flaw data $D_{21}$ and $D_{22}$ as discussed above represents the size of a flaw (knot).

With similar operation, flaw data $D_{31}$, $D_{32}$, $D_{41}$, $D_{42}$, $D_{51}$ and $D_{52}$ relating to foreign matter, a bubble, a drip are output from the flaw data generating portions CT3, CT4 and CT5.

As described above, flaw data $D_{11}$, $D_{12}$, ..., $D_{52}$ containing information representing the types and sizes of flaws are output from the electrical signal processing circuit 214, and sent to the flaw data acquisition circuit 215 (FIG. 8). In the following description, it is assumed that flaw data expressed by a pulse corresponds to a bit "1".

Next, the construction of the flaw data acquisition circuit 215 will be described.

Figure 17:
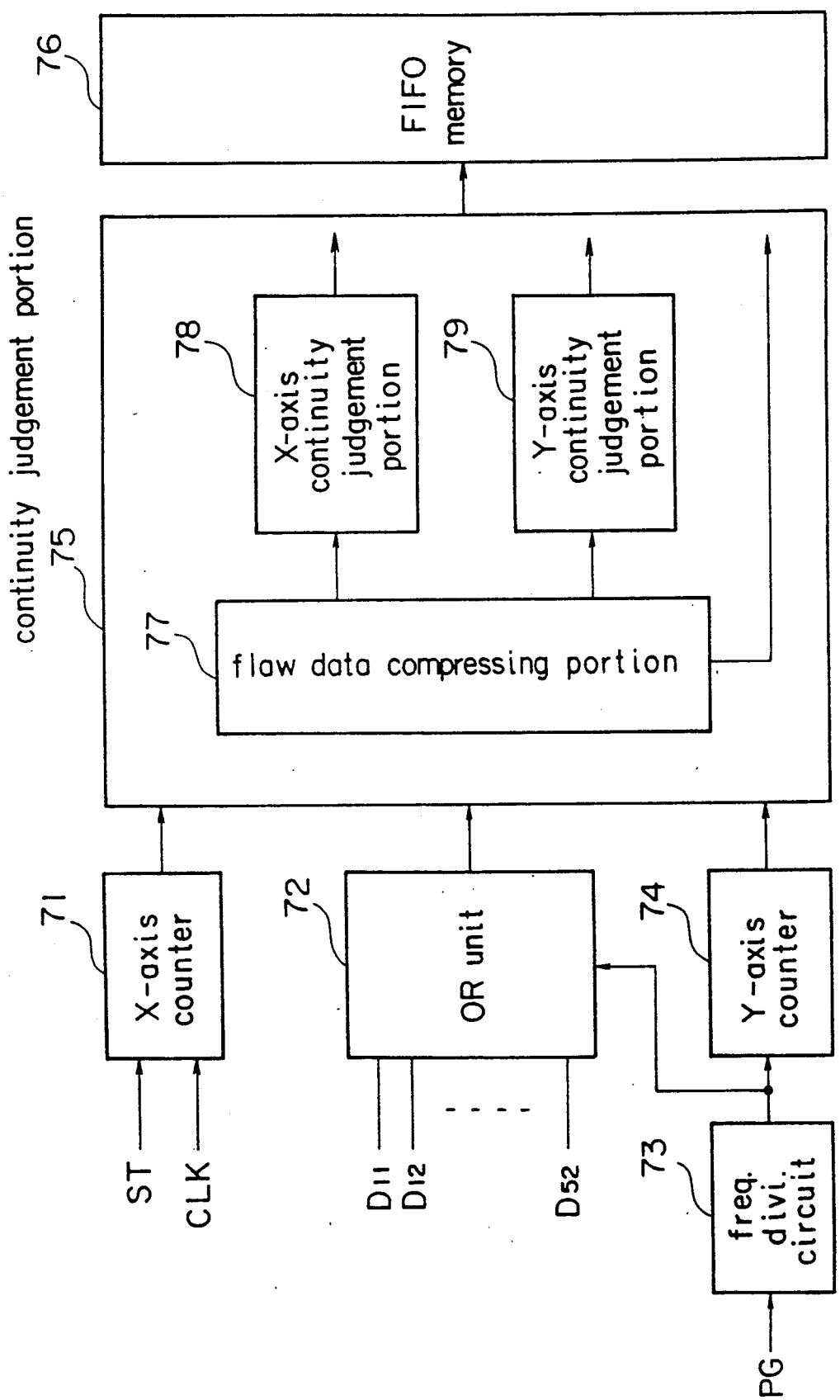
FIG. 17 is a block diagram illustrating a flaw data acquisition circuit.

FIG. 17 shows a typical construction of the flaw data acquisition circuit 215, which comprises an X-axis counter 71, an OR unit 72, a frequency division circuit 73, a Y-axis counter 74 and a coninuity judgement portion 75, and a FIFO memory 76; the continuity judgement portion 75 comprising a flaw data compressing portion 77, an X-axis continuity judgement portion 78, and a Y-axis continuity judgement portion 79.

The X-axix counter 71 is a counter that counts clock signals CLK for X-coordinate division, and is reset by a start pulse ST that is a start-to-scan signal. The start pulse ST is obtained in such a manner that the laser beam reflected by the rotating multiplanar mirror 223 of the flaw detector 220, as described above, is picked up at a given location via an optical fiber, converted photoelectrically to an electrical signal, and waveform-shaped. The X-axis counter 71 outputs a counter value at the time when the flaw data is collected, to the continuity judgement portion 75 as an X-coordinate location data.

The OR unit 72 is a unit which accumulates the flaw data for multiple scans from the electrical signal processing circuit, and outputs the flaw data at a predetermined timing.

The frequency division circuit 73 divides the frequency of a line synchronization signal PG corresponding to the moving distance along the line of a glass strip, as supplied by the pulse generator (not shown), and enters the frequency-divided line synchronization signal PG to the OR unit 72. The OR unit 72 outputs the accumulated flaw data at the timing of the frequency-divided line synchronization signal PG.

The Y-axis counter 74 counts the line synchronization signal PG frequency-divided by the frequency division circuit 73, and outputs the count value as Y-coordinate location data at the time when flaw data is input. The resetting of the Y-axis counter 74 is carried out through software processing.

Figure 18:
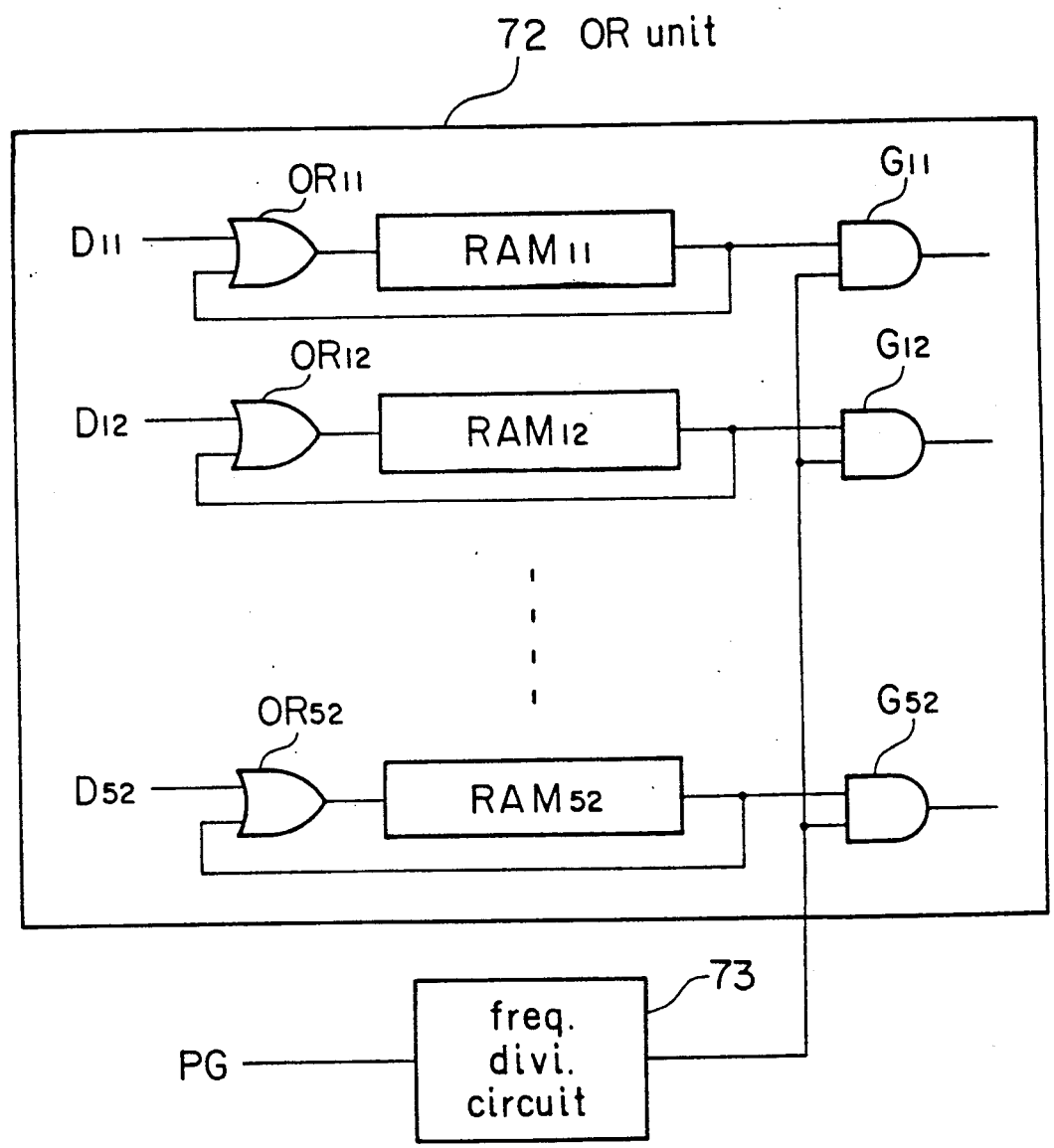
FIG. 18 is a circuit diagram of an OR unit.

FIG. 18 shows a typical example of the OR unit 72. The OR unit comprises logic OR circuits $OR_{11}$, $OR_{12}$, ..., $OR_{52}$ corresponding to flaw data $D_{11}$, $D_{12}$, ..., $D_{52}$ of multiple types, random access memories $RAM_{11}$, $RAM_{12}$, ..., $RAM_{52}$, and gate circuits $G_{11}$, $G_{12}$, ..., $G_{52}$.

Figure 19:
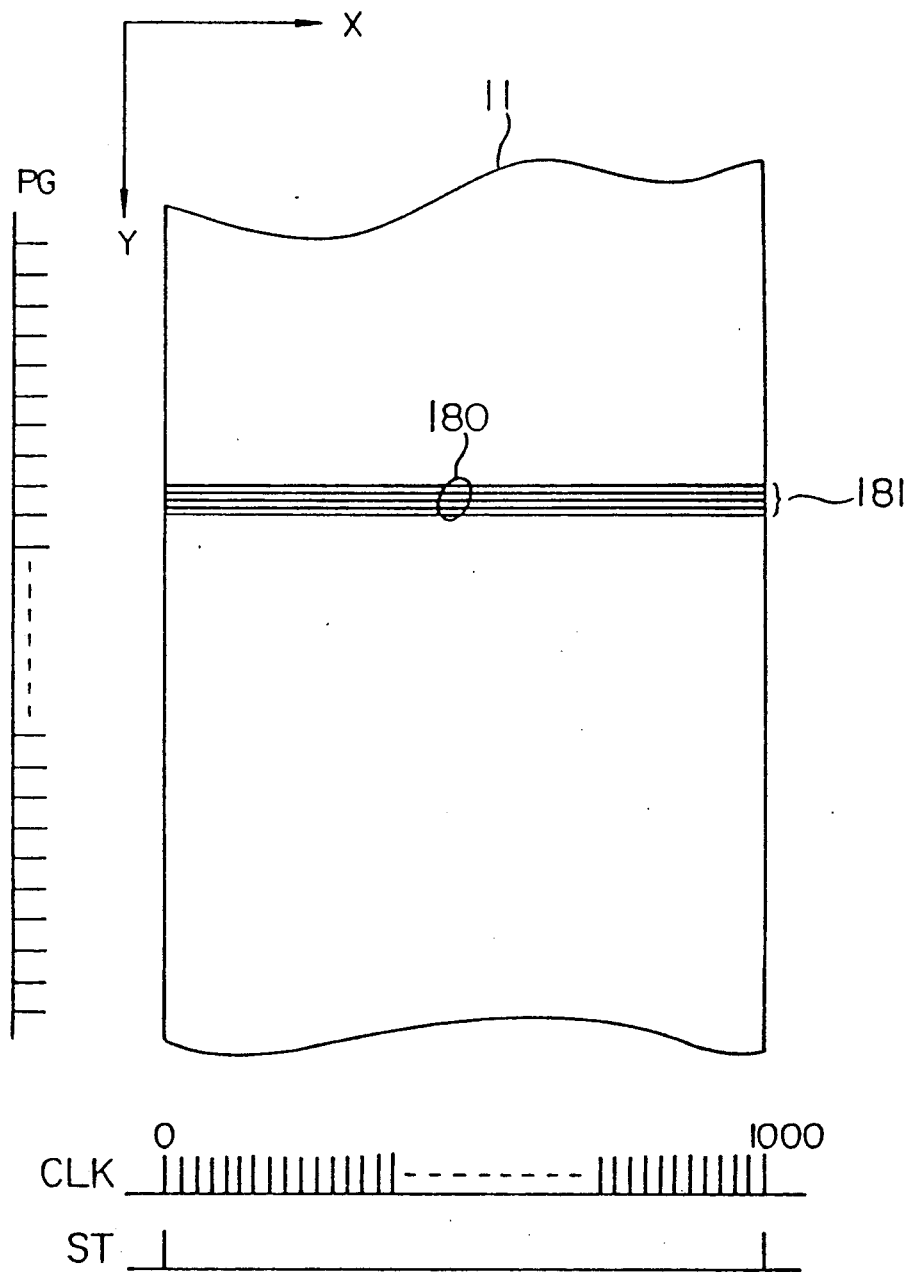
FIGS. 19 and 20 are diagrams of assistance in explaining the operation of the OR unit.
Figure 20:
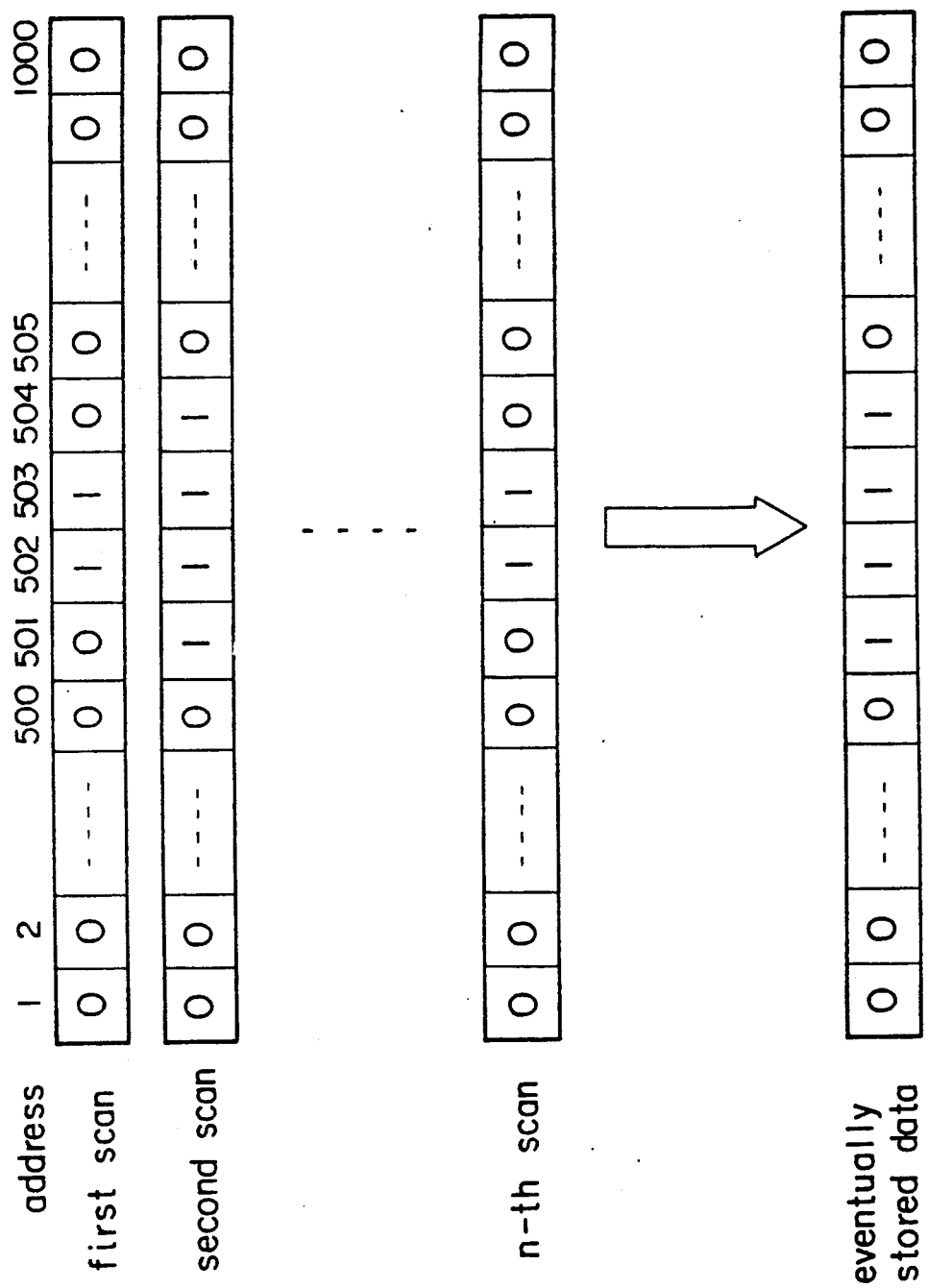

FIGS. 19 and 20 are diagrams of assistance in understanding the operation of the OR unit 72; FIG. 19 being a block diagram illustrating the relationship among scanning operation by a laser spot, a clock CLK and a frequency-divided line synchronization signal PG; and FIG. 20 being a diagram illustrating the state of accumulating flaw data $D_{11}$ in the $RAM_{11}$ of the OR unit. In the following, accumulation of the flaw data $D_{11}$ as an example of the functions of the OR unit will be described, reffering to these figures. It is now assumed that a glass strip is scanned n times in the X-axis direction by the laser beam spot during the line synchronization signal PG after frequency division. In FIG. 19, a scanning line by the laser beam spot is indicated by reference numeral 181. It is assumed that each RAM of the OR unit 72 has up to 1000 addresses. Each address in a RAM corresponds to the order of a clock CLK.

If there is a flaw 180 in the glass strip 11, as shown in FIG. 19, a flaw data $D_{11}$ entered from the electrical signal processing circuit at the first scan is written in the $RAM_{11}$, "1" bits are entered into the addresses 502 and 503, A flaw data $D_{11}$ entered at the second scan is ORed with the flaw data read from the $RAM_{11}$ in the logic OR circuit $OR_{11}$, and rewritten in the $RAM_{11}$, ..., and a flaw data $D_{11}$ entered at the n-th scan is ORed with the flaw data read from the $RAM_{11}$ in the logic OR circuit $OR_{11}$, and rewritten in the $RAM_{11}$. Thus, "1" bits are eventually stored in the addresses 501 to 504. In this way, the flaw data $D_{11}$ accumulated in the $RAM_{11}$ are output to the continuity judgement portion 75 via the gate circuit $G_{11}$ at the timing of the line synchronization signal PG frequency-divided in the frequency division circuit 73.

The continuity judgement portion 75 comprises a flaw data compressing portion 77 which compresses flaw data from the OR unit 72, an X-axis continuity judgement portion 78 which judges the X-axis continuity of the compressed data and outputs a start address and an end address in the X-axis direction, and a Y-axis continuity judgement portion 79 which judges the Y-axis continuity of the compressed data and outputs a start address and an end address in the Y-axis direction.

Figure 21:
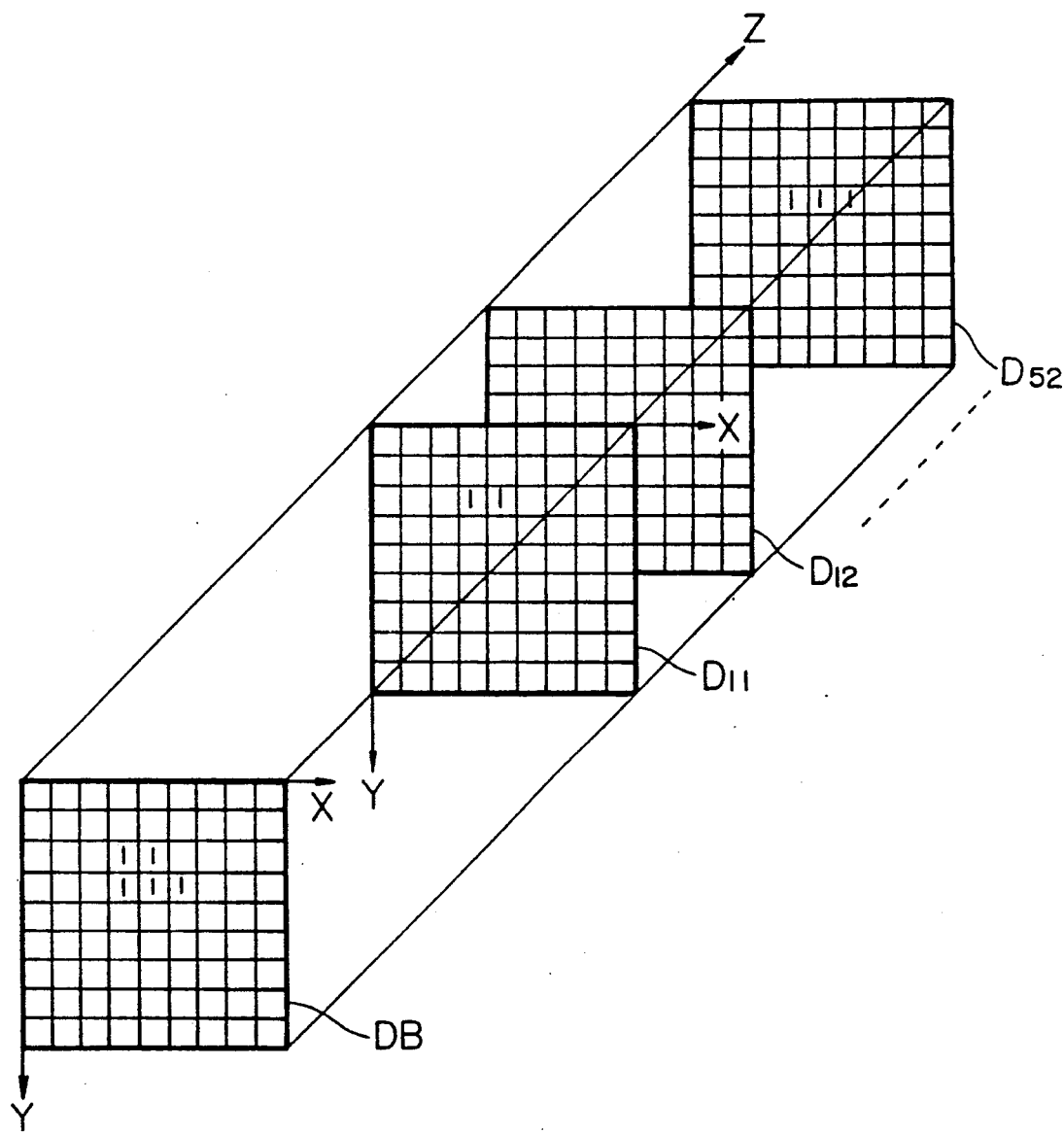
FIGS. 21, 22A and 22B are diagrams of assistance in explaining the operation of a continuity judgement portion.
Figure 22A:
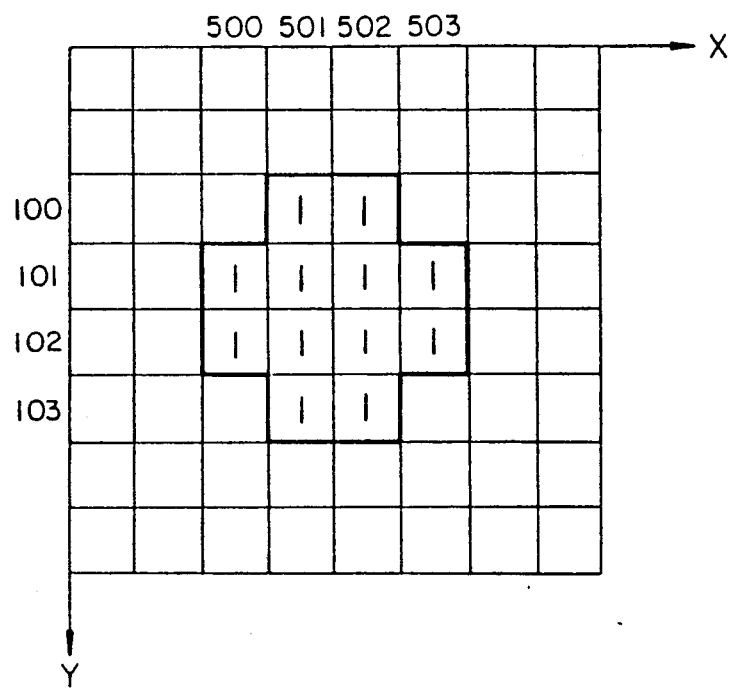
Figure 22B:
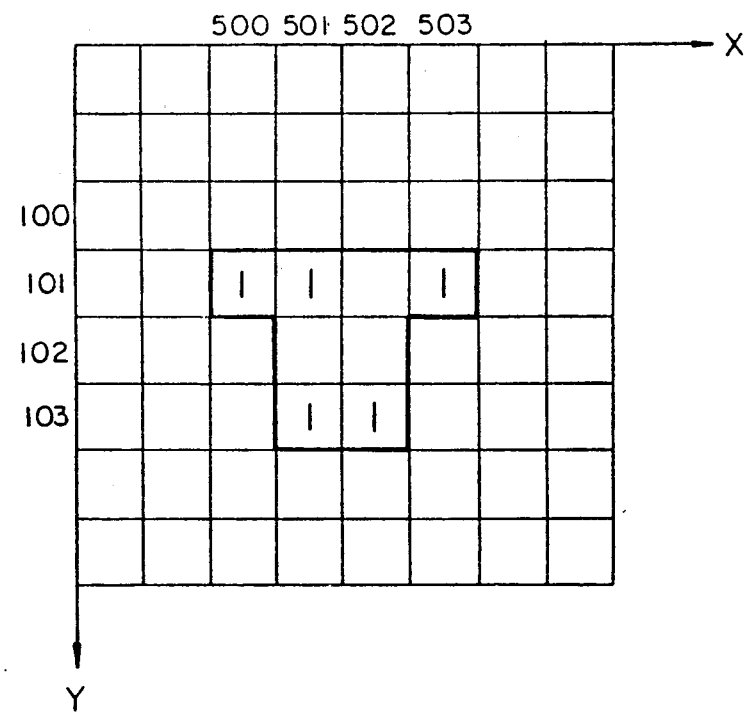

The operation of the continuity judgement portion 75 having the above-mentioned construction will be described, referring to FIGS. 21, 22A and 22B. FIG. 21 is a schematic diagram of assistance in explaining the operation of the flaw data compressing portion 77 which compresses flaw data. FIGS. 22A and 22B are diagrams illustrating bit patterns of the compressed flaw data to explain the operation of the X-axis continuity judgement portion 78 and the Y-axis continuity judgement portion 79.

As type-wise flaw data $D_{11}, D_{12}, \ldots, D_{52}$ are output by the OR unit 72, the flaw data for each type has a two-dimensional bit pattern in the X-axis address and Y-axis address directions. Assuming a three-dimensional space where the two-dimensionally arranged flaw data $D_{11}, D_{12}, \ldots, D_{52}$ are arranged in the Z-axis direction, it might be thought that three-dimensional flaw data groups $D_{11}, D_{12}, \ldots, D_{52}$ are output from the OR unit 72. The flaw data compressing portion 77 forms a compressed two-dimensional flaw data DB by ORing in the Z-axis direction the entire three-dimensional flaw data groups $D_{11}, D_{12}, \ldots, D_{52}$ arranged in the X-axis and Y-axis addresses. In FIG. 21, "1" bits are present only in the flaw data $D_{11}$ and the flaw data $D_{52}$.

FIGS. 22A and 22B show an example of the bit pattern of the flaw data compressed based on the following concept.

The X-axis continuity judgement portion 78 and the Y-axis continuity judgement portion 79 check the continuity of "1" bits in the X-axis and Y-axis directions, respectively, and check the presence or absence of a discontinuity in "1" bits. Based on parameters, both portions 78 and 79 determine whether the detected discontinuity be combined in the X-axis direction or in the Y-axis direction.

FIG. 22A shows a flaw data block synthesized by a continuity judgement process when all the parameters of the X-axis continuity judgement portion 78 and the Y-axis continuity judgement portion 79 are zero. The X-axis continuity judgement portion 78 outputs the address 500 as an X-axis start address for this flaw data block and the address 503 as an X-axis end address, while the Y-axis continuity judgement portion 79 outputs the address 100 as a Y-axis start address for the flaw data block and the address 103 as a Y-axis end address.

FIG. 22B shows a flaw data block synthesized by a continuity judgement process when all the parameters of the Y-axis continuity judgement portion 78 and the Y-axis continuity judgement portion 79 are 1. When the parameters are 1, even when there is a discontinuity in an address, the discontinuity is combined to form a flaw data block shown in the figure. In this case, the X-axis continuity judgement portion 78 outputs the address 500 as and X-axis start address for this flaw data block, and the address 503 as an X-axis end address. The Y-axis continuity judgement portion 79, on the other hand, outputs the address 101 as a Y-axis start address for the flaw data block and the address 103 as a Y-axis end address. By performing continuity judgement in which discontinuities in "1" bits are combined by interpolation, it is made possible to identify these flaw data as the flaw data for a single flaw even if such flaw data are generated from a plurality of light receptors at shifted timings when a single flaw is scanned by the laser beam spot.

At the time when the continuity of "1" bits is broken, the Y-axis continuity judgement portion 79 outputs "1" bits, which represent the type of the flaw data, as a flow pattern to the FIFO memory 76, and both the X-axis continuity judgement portion 78 and the Y-axis continuity judgement portion 79 output the X-axis start and end addresses and the Y-axis start and end addresses of the flaw data block as flaw location data to the FIFO memory 76. The Y-axis continuity judgement portion 79 has a function of forcibly cutting the Y-axis continuity of "1" bits if the continuity extends beyond a predetermined length and outputting a flaw pattern and location information to the FIFO memory 76.

The FIFO memory 76 stores these flaw patterns and location data fed by the X-axis and Y-axis continuity judgement portions 78 and 79 to transfer to the memory of the information processing device 217 by direct memory access.

Figure 23:
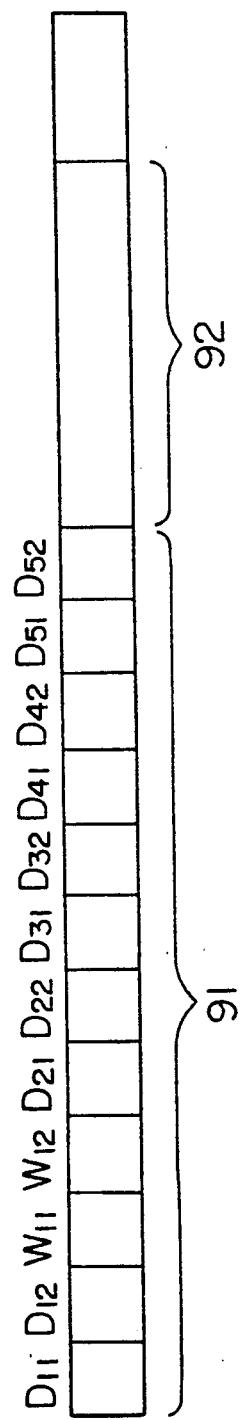
FIG. 23 is a diagram illustrating a format of the data output from the flaw data acquisition circuit.

FIG. 23 shows a format of the data transferred from the flaw data acquisition circuit 215 to the information processing device 217. This data consists of a flaw pattern 91 comprising a bit train representing the type and size of a single flaw in a glass plate, and location data 92 representing the location of the flaw.

The information processing device 217 has a flaw discriminating pattern table 216 for judging the type, size, etc. of the flaw, with which the flaw pattern fed from the flaw data acquisition circuit 215 to discriminate the type, size, etc. of the flaw, and the location of the flaw from the information on location fed from the flaw data acquisition circuit 215, and sends these discriminating results to the control unit 102 (FIG. 1) which controls the sorting process based on the information supplied.

INDUSTRIAL APPLICABILITY

The glass-plate sorting system of this invention makes it possible to improve yield in the manufacture of glass plates by detecting the sizes and locations of flaws existing in a glass strip by means of a discriminating-type flaw detector of high precision, tracking the flaws by a control unit, and sorting quality grades of the glass plates being cut so as to simultaneously obtain a desired number of products of specified quality grades.

When used in the manufacturing line of automotive windshields, the glass-plate sorting system of this invention makes it possible to improve yield in the manufacture of automotive windshields by detecting the sizes and locations of flaws existing on a glass strip by a discriminating-type flaw detector of high precision, tracking the flaws by a control unit, and judging the acceptability of glass plates being cut by establishing criteria for quality grades in the see-through and peripheral areas of windshields on the glass plates being cut.

It is claimed

1. A glass-plate sorting system for cutting a glass strip travelling on a line coveyor and sorting the quality grades of glass plates being cut comprising:

a discriminating-type flaw detector for detecting flaws existing in the glass strip and outputting flaw data information representing the types, sizes and locations of the flaws, said discriminating-type flaw detector including light-spot scanning means for scanning the glass strip with a light spot, light-receiving means having a plurality of light receptors each of said light receptors receiving more than two types of light among transmitted light, transmitted and diffused light, reflected light and reflected and diffused light form the glass strip scanned by the light spot, photoelectric converting means having a plurality of photoelectric converters each connected to each of the light receptors for converting light received by the corresponding light receptor into an electrical signal, electrical signal processing means for processing the electrical signal from the photoelectric converting means to generate flaw data containing information on the types and sizes of flaws existing in the glass strip, flaw data acquisition means for collecting flaw data from the electrical signal processing means, combining and processing the collected flaw data to form a flaw pattern indicating the types and sizes of flaws and including flaw location data, and information processing means for comparing the flaw pattern with a flaw discriminating pattern table stored in advance to discriminate the types and sizes of flaws and discriminate flaw locations based on the flaw location data;

a control unit for sorting the quality grades of the glass plate being cut based on the flaw data information from the discriminating-type flaw detector; and a plurality of sorters for sorting glass plates of desired quality grades based on the control of the control unit.

2. A glass-plate sorting system as set forth in claim 1, wherein the light spot scanning means comprises:

a light source for generating a light beam;

light projecting means for repeatedly projecting the light beam from the light source as the light spot onto the glass strip in the direction normal to the travelling direction of the glass strip.

3. A glass-plate sorting system as set forth in claim 2, wherein at least light receptors each for receiving each of transmitted light and transmitted and diffused light among the light receptors comprises a plurality of optical fibers, one ends of which are arranged in a row to constitute a light-receiving surface, and the other ends of which are connected to the photoelectric converting means.

4. A glass-plate sorting system as set forth in claim 3, wherein the flaw data acquisition means comprises:

a first counter for counting a first pulse train relating to the location of the glass strip in the direction normal to the travelling direction thereof and outputting a count value at the time when flaw data is collected;

a second counter for counting a second pulse train relating to the location of the glass strip in the travelling direction thereof and outputting a count value at the time when flaw data is collected;

an OR unit for accumulating and OR-processing flaw data for a plurality of scans and outputting processed flaw data at the pulse generating timing of the second pulse train;

a continuity judgement circuit for compressing flaw data from the OR unit, judging the continuity of the compressed flaw data in the travelling direction and in the direction normal to the travelling direction thereof, and synthesizing a flaw data block; and a buffer memory for temporarily storing the output of said continuity judgement circuit.

5. A glass-plate sorting system as set forth in claim 1, wherein the control unit discriminates the glass plates being cut into three types: high-grade plates, low-grade plates, and defective plates; and the sorters perform a two-grade sorting by sorting high-grade and low-grade products.

6. A glass-plate sorting system as set forth in claim 5, wherein the sorters have lifters installed below the line conveyor for pushing up glass plates, and suction conveyors installed above the line conveyor for sucking and carrying the pushed-up glass plates.

7. A glass-plate sorting system as set forth in claim 1 for use in automotive windshield manufacturing processes, wherein the control unit establishes quality grades that can be accepted as good products on an area of the glass plates corresponding to a see-through area of an automotive windshield and an area of the glass plates corresponding to a peripheral area outside the seethrough area, and discriminates glass plates of acceptable quality by comparing the sizes and locations of the detected flaws with the established quality grades for these areas.

* * * * *